(12) United States Patent
Srouji

(10) Patent No.: US 11,077,235 B2
(45) Date of Patent: Aug. 3, 2021

(54) FAT-DEPLETED ADIPOSE TISSUE AND A DEVICE AND METHOD FOR PREPARING THE SAME

(71) Applicants: Samer Srouji, Haifa (IL); Zohar Gendler, Zichron-Yaakov (IL)

(72) Inventor: Samer Srouji, Haifa (IL)

(73) Assignees: Samer Srouji, Haifa (IL), part interest; Zohar Gendler, Zichron-Yaakov (IL), part interest (*) Notice: Subject to any disclaimer, the term of this patent is extended or adjusted under 35 U.S.C. 154(b) by 162 days.

(21) Appl. No.: 15/571,432

(22) PCT Filed: May 5, 2016

(86) PCT No.: PCT/IL2016/050474
§ 371 (c)(1),
(2) Date: Nov. 2, 2017

(87) PCT Pub. No.: WO2016/178230
PCT Pub. Date: Nov. 10, 2016

(65) Prior Publication Data
US 2019/0009007 A1    Jan. 10, 2019

Related U.S. Application Data

(60) Provisional application No. 62/156,935, filed on May 5, 2015.

(51) Int. Cl.
*B30B 9/04* (2006.01)
*B30B 9/06* (2006.01)
(Continued)

(52) U.S. Cl.
CPC .......... *A61M 1/0011* (2013.01); *A61K 35/28* (2013.01); *A61K 35/32* (2013.01); *A61K 35/35* (2013.01);
(Continued)

(58) Field of Classification Search
CPC .. B30B 9/04; B30B 9/045; B30B 9/06; B30B 9/10; B30B 15/08; B30B 15/22;
(Continued)

(56) References Cited

U.S. PATENT DOCUMENTS 2,818,797 A     1/1958   Ballor
4,306,436 A  *  12/1981  Schulz ................. B21D 26/055
                                                                100/269.04
(Continued)

FOREIGN PATENT DOCUMENTS

WO         2011117821 A1     9/2011

OTHER PUBLICATIONS

Rada, T. et al., "Adipose tissue-derived stem cells and their application in bone and cartilage tissue engineering.", Tissue Engineering Part B: Reviews, vol. 15, No. 2, (Jan. 27, 2009), pp. 113-125, URL: http://online.liebertpub.com/doi/abs/10.1089/ten.teb.2008.0423, XP055295141 [Y] 16-18, 20-22 *Table 1, p. 117, left hand column last paragraph and the rest of the section up to p. 118, pp. 119-120.

(Continued)

*Primary Examiner* — Jimmy T Nguyen
(74) *Attorney, Agent, or Firm* — William Dippert; Laurence Greenberg; Werner Stemer

(57) ABSTRACT

A device configured to mechanically remove a fat phase from at least one adipose tissue includes a first pressing element and a second pressing element. Furthermore, there is provided a method for preparing a preparation including a fat-depleted adipose tissue, the method including mechanically removing a fat phase from at least one adipose tissue. In addition, there is provided a preparation including a fat-depleted adipose tissue, wherein the fat-depleted adipose tissue is prepared by mechanically removing a fat phase from at least one adipose tissue.

13 Claims, 9 Drawing Sheets

(51) Int. Cl.
  *A61M 1/00* (2006.01)
  *A61K 35/32* (2015.01)
  *A61K 35/35* (2015.01)
  *A61K 35/28* (2015.01)
  *B30B 15/08* (2006.01)
  *B30B 15/22* (2006.01)

(52) U.S. Cl.
  CPC .............. *A61M 1/0066* (2013.01); *B30B 9/04* (2013.01); *B30B 9/06* (2013.01); *B30B 15/08* (2013.01); *B30B 15/22* (2013.01); *A61M 2202/08* (2013.01)

(58) Field of Classification Search
  CPC .............. A61M 1/0011; A61M 1/0066; A61M 2202/08; A61K 35/35; A61K 35/28; A61K 35/32
  USPC .................. 100/94, 98 R, 110, 126, 127
  See application file for complete search history.

(56) References Cited

U.S. PATENT DOCUMENTS

| | | |
|---|---|---|
| 4,958,557 A | 9/1990 | Fiala |
| 5,172,630 A * | 12/1992 | Thompson ............ B30B 9/3075 100/193 |
| 6,194,017 B1 * | 2/2001 | Woodward ............ A21C 11/12 425/290 |
| 8,936,651 B2 | 1/2015 | Yang et al. |
| 9,192,939 B2 | 11/2015 | Tremolada |
| 2003/0161816 A1 * | 8/2003 | Fraser ...................... A61P 1/00 424/93.7 |
| 2009/0283482 A1 * | 11/2009 | Owen .................... A47J 36/20 210/774 |
| 2010/0124776 A1 | 5/2010 | Shi |
| 2010/0282091 A1 * | 11/2010 | Doleac ............... B65D 85/8043 99/295 |
| 2010/0326293 A1 * | 12/2010 | Derubeis .................. B30B 9/04 100/37 |
| 2012/0100611 A1 | 4/2012 | Kensy et al. |
| 2013/0255510 A1 | 10/2013 | Kassis |
| 2014/0017783 A1 | 1/2014 | Gimble et al. |
| 2015/0093362 A1 * | 4/2015 | Dominguez ........ A61L 27/3604 424/93.7 |

OTHER PUBLICATIONS

Diekman, B. O. et al., "Chondrogenesis of adult stem cells from adipose tissue and bone marrow: induction by growth factors and cartilage-derived matrix.", Tissue Engineering Part A, vol. 16, No. 2, (Aug. 29, 2009), pp. 523-533, URL: http://online.liebertpub.com/doi/abs/10.1089/ten.tea2009.0398, XP055109930 [Y] 16-18, 20-22 * p. 524, section titled "Cell culture and chondrogenic differentiation" *.

Raposio, E. et al., "A novel and effective strategy for the isolation of adipose-derived stem cells: minimally manipulated adipose-derived stem cells for more rapid and safe stem cell therapy", (Jun. 30, 2014), XP009502188 [X] 10, 11, 14, 19 * "Materials and Methods" section, p. 1406 and Figure 1 "Materials and Methods" section, p. 1406 and Figure 1* [Y] 16-18, 20-22.

* cited by examiner

FAT-DEPLETED ADIPOSE TISSUE AND A DEVICE AND METHOD FOR PREPARING THE SAME

CROSS-REFERENCE TO RELATED APPLICATIONS

This application is a National Phase filing under 35 U.S.C. § 371 of International Patent Application No. PCT/IL2016/050474, filed May 5, 2016, which is based upon and claims the benefit of the priority date of U.S. Provisional Patent Application Ser. No. 62/156,935, filed May 5, 2015, each of which is incorporated herein by reference.

FIELD OF THE INVENTION

The present invention relates to tissue regeneration. More particularly, the present invention relates to the provision of preparations for bone and soft tissue regeneration.

BACKGROUND OF THE INVENTION

A bone is a rigid organ that constitutes part of the vertebral skeleton. Bones serve multiple functions, including support and protection of organs of the body, production of red blood cells and lymphocytes, storage of minerals and enablement of mobility of the body. Bones are lightweight yet strong and hard, come in a variety of shapes and sizes and have a complex internal and external structure. There are two types of bone tissue in a bone: cortical and cancellous. The cortical bone tissue forms the cortex, or outer shell of the bone. It is a compact, dense, hard, strong and stiff tissue, filled with a mineralized matrix made of an organic component, mainly collagen, and an inorganic component of bone mineral made up of various salts, mainly salts of calcium and phosphate. In the mineralized matrix there are tiny spaces, termed lacunae, which contain bone cells. The cancellous tissue is found in the marrow space (medullary cavity) of the bone, and has a sponge-like appearance with numerous large spaces. Other types of tissue found in bones include marrow—where red blood cells and lymphocytes are produced, endosteum—the tissue lining the medullary cavity of the cone, periosteum—a thin connective tissue that covers the surface of the bone, nerves, blood vessels and cartilage.

There are four types of bone cells in a bone: osteoblasts, osteocytes, lining cells and osteoclasts.

The osteoblasts are mononucleate small cells that are responsible for the formation of bone tissue, and thus have an important role in bone formation, remodeling and repair. During bone formation, osteoblasts first secret a unique collagen-rich extracellular matrix, which serve as a framework on which mineralization of the bone tissue is taking place by deposition of calcium phosphate, which is then hardened by hydroxide and bicarbonate ions. During bone formation, some osteoblasts are trapped in the hardened bone tissue, while others remain on top of the new bone tissue.

Osteocytes are osteoblasts that were trapped in the newly formed bone tissue. They reside in tiny spaces in the bone tissue, termed lacunae. Osteocytes communicate with each other through long cellular extensions, sense mechanical stress in the bone, and send signals to the osteoblasts for bone remodeling as a result of mechanical stress.

Lining cells are osteoblasts that remained on top of the new bone tissue, and used to protect the underlying bone tissue.

Osteoclasts are multinucleate large macrophage-like cells that are responsible for the breakdown of bones. Osteoclasts resorb bones by a combination of localized acidification for removing the minerals and protease secretion for breaking down the collagen matrix. Osteoclasts that tunnel through the bone are usually followed close behind by osteoblasts, which form a new bone tissue. This remodeling process is very important for bone health. Therefore, because of its importance in bone remodeling, the breakdown of bones is controlled by hormones, which instruct the osteoclasts when and where to break down bone tissue.

Bone formation takes place during fetal development of the skeletal system and wound healing. Two distinct processes are involved in bone formation: endochondral ossification and intramembranous ossification. During the endochondral ossification cartilage is first formed by mesenchymal progenitor cells. Then, cartilage cells, known as chondrocytes, undergo hypertrophy and the extracellular matrix mineralizes. Then, blood vessels invade the newly formed tissue, bringing cells that degrade the existing cartilage matrix. Afterwards bone tissue is formed by osteoprogenitor cells. Long bones are formed by endochondral ossification during fetal development. On the other hand, intramembranous ossification is a more direct process, in which osteoprogenitor cells form bone tissue directly. Carnial bones are formed by intramembranous ossification during fetal development. Wound healing in a bone may proceed with either process, depending on local environmental factors, including how much the ends of the bone can move relative to each other. For example, in cases when the ends of the bone can significantly move relative to each other, endochondral ossification is favored.

Osteoprogenitor cells have the ability to differentiate into osteoblasts or chondrocytes, depending on the signaling molecules they are exposed to, giving rise to either bone or cartilage, respectively. These cells reside in the periosteum and the marrow of a bone. The osteoprogenitor cells are progenitor cells that arise from mesenchymal stem cells.

Bone regeneration is a complex physiological process of bone formation occurring during normal fracture healing and is involved in continuous bone remodeling. However, there are complex clinical conditions in which bone regeneration is required in a large extent, for example during skeletal reconstruction of large bone defects created by major trauma, infection, tumor resection or skeletal abnormalities; or in cases in which the regenerative process is compromised, for example vascular necrosis, atrophic nonunion and osteoporosis.

In some cases, such as dental reconstruction and nonunion fracture, there may be enough progenitor cells in the damaged area that may be stimulated to induce local bone formation. However, in other cases, for example a compromised site, such as where a tumor was removed and the local tissue was irradiated, there may not be enough local progenitor cells to induce local bone formation. Also an alternative approach, such as releasing growth factors in the damaged site in order to induce the formation of progenitor cells, in a site where a tumor was removed, may not be a good idea.

Another approach is soft tissue regeneration, which includes for example gum tissue grafts such as connective tissue grafts, free gingival grafts and pedicle grafts. There are cases in which tissue-stimulating proteins are used to encourage the natural ability of the body to support growth of the tissue.

An example of a soft tissue regeneration procedure is gingival reconstruction. The gingiva surrounding a tooth has a 2-3 mm band of bright pink, very strong attached mucosa, then a darker, larger area of unattached mucosa that fold into the cheeks. When replacing a tooth with an implant, a band of strong, attached gingiva is needed to keep the implant healthy in the long-term. This is especially important with implants because the blood supply is more precarious in the gingiva surrounding an implant, and is theoretically more susceptible to injury because of a longer attachment to the implant than on a tooth (a longer biologic width). When an adequate band of attached tissue is absent, it can be recreated with a soft tissue graft.

According to Rozalia Dimitriou et al (2011): "Currently, there is a plethora of different strategies to augment the impaired or 'insufficient' bone-regeneration process, including the 'gold standard' autologous bone graft, free fibula vascularized graft, allograft implantation, and use of growth factors, osteoconductive scaffolds, osteoprogenitor cells and distraction osteogenesis. Improved 'local' strategies in terms of tissue engineering and gene therapy, or even 'systemic' enhancement of bone repair, are under intense investigation in an effort to overcome the limitations of the current methods, to produce bone-graft substitutes with biomechanical properties that are as identical to normal bone as possible, to accelerate the overall regeneration process, or even to address systemic conditions, such as skeletal disorders and osteoporosis." (Rozalia Dimitriou, Elena Jones, Dennis McGonagle and Peter V. Giannoudis. BMC Medicine, 2011, 9:66 doi:10.1186/1741-7015-9-66).

In general, current clinical treatments for critical-sized bone defects are problematic and often yield poor healing due to the complicated anatomy and physiology of bone tissue, as well as the limitations of medical technology.

Bone regeneration procedures include procedures such as correction defects in bones (caused by traumas, diseases etc.); adding missing bone parts; spinal fusion surgery; and maxillary sinus lifting procedure. In addition, the bone regeneration procedure may include the usage of cages.

General applications of bone regeneration include: healing of nonunion fractures; craniofacial reconstruction; healing of segmental defects due to tumor removal or trauma; augmentation of bone around hip implants revision; and spinal fusion.

Applications of bone regeneration in dental procedures include: building up bone tissue around implants placed in tooth sockets after tooth extraction; socket preservation for future implantation of false teeth or prosthetics; filling of bone defects after removal of the root of a tooth, cystectomy or removal of impacted teeth; and repairing bone defects after reopening of a wound.

One example of bone regeneration procedure is a sinus lifting. A sinus lift is a bone grafting procedure typically done when the bone in a patient's upper jaw is too thin to securely hold dental implants. The procedure involves significant trauma. Six to nine months after the procedure, new bone is generated.

Bone tissue engineering offers a promising alternative strategy of healing severe bone injuries by utilizing the body's natural biological response to tissue damage in conjunction with engineering principles. Osteogenic cells, growth factors, and biomaterial scaffolds form the foundation of the many bone tissue engineering strategies employed to achieve repair and restoration of damaged tissue. An ideal biomaterial scaffold will provide mechanical support to an injured site and also deliver growth factors and cells into a defect to encourage tissue growth. Additionally, this biomaterial should degrade in a controlled manner without causing a significant inflammatory response.

An important element for bone regeneration is having a source that will provide viable cells that can differentiate and proliferate into osteogenic cells. For a long time, autologous bone graft has been used and considered as the gold standard material for bone regeneration in orthopedic surgery. Autologous bone is usually harvested from the anterior and posterior iliac crests of the pelvis. It can also be harvested as vascularized bone graft containing an internal vascular network in order to restore a significant bone defect, or tricortical graft for structural support. Although autologous bone graft is a safe and effective way to provide bone cells still it has multiple limitations including donor site morbidity, limited cells quantity, requirement of a second surgical procedure with frequent consequences of pain, and complications (Mina W. Morcos, Hadil Al-Jallad and Reggie Hamdy, 2015, Review article—Comprehensive Review of Adipose Stem Cells and Their Implication in Distraction Osteogenesis and Bone Regeneration, BioMed Research International, Volume 2015, Article ID 842975, http://dx.doi.org/10.1155/2015/842975, referred to hereinafter as Morcos et al, 2015).

An alternative method to harvest autologous bone graft is reamer irrigation aspiration system. Reamer irrigation aspiration is an intramedullary reaming system that provides continuous irrigation and aspiration during intramedullary reaming. It was originally designed to decrease the adverse effects of reaming long bone fractures by collecting the reaming material which contains a significant number of osteogenic cells. This provides a large volume of cortico-cancellous bone material that can be used as autologous bone graft. This is usually harvested from the femur [89]. This technique provides a large volume of autologous bone graft that corresponds to the bone graft obtained from both the anterior and posterior iliac crest; however it still has similar limitations regarding the need for a second operation and the limited quantity of cells that can be provided (Morcos et al, 2015).

Another method would be allograft bone that is available in different preparations. However, allograft bone lacks osteogenic capacity as it does not contain living bone cells; therefore it is not considered to be a good source for osteogenic cells. Moreover it carries the risk of disease transmission and immunogenic responses (Morcos et al, 2015).

Since both autograft and allograft have restrictions, the use of mesenchymal stem cells has been considered.

Mesenchymal stem cells are multipotent stromal cells than can differentiate and proliferate into a variety of cell types, including: chondrocytes (cartilage cells), myocytes (muscle cells), adipocytes (fat cells), and osteogenic cells under the appropriate molecular signals. Mesenchymal stem cells have been found in multiple tissues including bone marrow and adipose tissues, and growth factors may be used to enhance cell proliferation and differentiation of mesenchymal stem cells into osteogenic lineage (Morcos et al, 2015).

Stem cells are undifferentiated progenitor cells that are capable of both self-renewal and multilineage differentiation. They are classified into two categories, depending on their origin: the embryonic stem cells and adult stem cells. Adult stem cells are derived from differentiated postnatal tissues and are believed to be intimately involved in tissue and organ regeneration and repair during injury and ageing. Adult stem cells are considered to be multipotent since they have a low degree of plasticity (Morcos et al, 2015).

Mesenchymal stem cells are a type of adult stem cells, which were initially discovered in bone marrow, but afterwards were isolated and characterized from several adult and fetal tissues, including adipose tissue, dermis, periosteum, umbilical cord blood, placenta and amniotic fluid, and synovial fluid. Mesenchymal stem cells have significant therapeutic potentials that can be applied to multiple disciplines especially where Mesenchymal stem cells show low immunogenicity. Mesenchymal stem cells can differentiate into osteoblasts, chondroblasts, and adipocytes (Morcos et al, 2015).

Adipose derived mesenchymal stem cells are able to differentiate into multiple lineages, in particularly chondrocytes, osteocytes, and adipocytes, when the correct conditions are provided. The induction of Adipose derived mesenchymal stem cells differentiation in vitro is achieved by culturing Adipose derived mesenchymal stem cells in specific media. Another practice to differentiate Adipose derived mesenchymal stem cells is the application of physical stimuli including mechanical forces, magnetic, and electrical fields (Morcos et al, 2015).

Adipose derived mesenchymal stem cells are isolated from lipoaspirates. One gram of adipose tissue yields approximately $3 \times 10^5 - 1 \times 10^6$ mesenchymal stem cells, which is 500-fold greater than the number of mesenchymal stem cells in one gram of bone marrow. Adipose derived mesenchymal stem cells possess several advantages when compared to bone marrow mesenchymal stem cells. First, Adipose derived mesenchymal stem cells are readily available in large quantities, almost unlimited, and can be retrieved in high volumes of cellular population with less invasive methods such as liposuction aspirates or subcutaneous adipose tissue fragments. Moreover, Adipose derived mesenchymal stem cells can easily be expanded in vitro, have an extensive self-renewal capacity, and are easily isolated in a laboratory setting by differential sedimentation. Adipose derived mesenchymal stem cells can differentiate into various types of cells, including adipocytes, osteoblasts, and chondrocytes (Morcos et al, 2015).

Adipose tissue is comprised of adipocytes and a heterogeneous set of cell populations including endothelial cells, endothelial progenitor cells, pericytes, and erythrocytes that surround and support them, which upon isolation are termed the stromal vascular fraction. In order to isolate adipose derived mesenchymal stem cells, adipose cells are harvested and then minced and digested by collagenase type II. Then the stromal vascular fraction is separated by centrifugation as it has a higher density than the adipocytes. Later on, isolate adipose derived mesenchymal stem cells are isolated from the stromal vascular fraction by plastic adherence in culture, which can easily be cultured and expanded in vitro. Moreover, isolated adipose derived mesenchymal stem cells can be cryopreserved in a media of serum and dimethyl sulfoxide without losing their ability to differentiate and proliferate (Morcos et al, 2015).

Several approaches for isolating adipose derived mesenchymal stem cells from an adipose tissue, and for using the isolated adipose derived mesenchymal stem cells for soft tissue or bone tissue regeneration, are known in the art.

One approach involves the use of enzymes. For example, United States patent application publication No. US 2008/0095750 A1 describes a procedure for isolating adult stem cells from human liposuction tissue, the procedure comprises collagenase digestion of the liposuction tissue, differential centrifugation and expansion in culture. Similarly, United States patent application publication No. US 2015/0037289 A1 describes a method for preparing a stem cells preparation for treating a bone, ligament, tendon or cartilage injury in an animal, the method comprising: collecting adipose tissue from a source animal, contacting the adipose tissue with an enzyme preparation, including collagenase and protease, that digests fat and connective tissues contained in the adipose tissue, while preserving the stem cells in the adipose tissue, and collecting the stem cells. Afterwards, blood is collected from the same source animal and used for the preparation of platelet rich plasma, which is mixed with the collected stem cells in order to activate the stem cells.

Enzymes such as collagenase are typically used to dissolve the bonds in the collagen that hold together the adipose tissue (see, for example, Zuk, et al. Mol Biol Cell. 2002; 13: 4279-4295; Zuk, et al. Tissue Eng. 2001; 7: 211-228). While collagenase is effective, it can be unsuitable for preparing stem cells for the following reasons:

enzyme treatment results in a high level of cell death, thereby reducing numbers of isolated stem cells and resulting in more cellular debris;

enzymes may damage and destroy unique cell types;

contamination of isolated stem cells with enzymes may make them unsuitable for transplantation; and regulatory bodies may consider that the use of enzymes in the isolation of stem cells results in a cellular product requiring drug approval.

Another approach is in vitro culturing of isolated adipose derived mesenchymal stem cells with specific growth media for differentiating the stem cells for a desired cell type. For example, U.S. Pat. No. 6,777,231 B1 describes inter alia obtaining raw liposuction aspirate from a patient, rinsing the liposuction aspirate, digesting with collagenase, centrifuging, treating a cellular pellet with an erythrocyte-lysing solution, and isolating the obtained stem cells by centrifugation. Then, a population of isolated adipose derived stem cells was cultured at high density in a chondrogenic medium for several weeks. In addition, a population of isolated adipose derived stem cells was cultured until near confluence and then exposed to an osteogeneic medium for several weeks.

Yet another approach involves the use of wave energy. For example, United States patent application publication No. US 2006/0051865 A1 describes methods for isolating cells from adipose tissue that have potential to differentiate into cells of mesenchymal origin, the methods comprise subjecting adipose tissue to an electromagnetic, sonic, or other wave energy source, and centrifuging the tissue to form a pellet comprising stem cells. Also United States patent application publication No. US 2015/0231244 A1 describes an adipose-derived stem cell processing system comprising inter alia an ultrasonic generator configured to excite a raw adipose tissue with ultrasonic energy for isolating adipose-derived stem cells from the raw adipose tissue.

The currently known methods, devices and systems for isolating adipose derived mesenchymal stem cells from an adipose tissue for soft tissue or bone tissue regeneration—are cumbersome, expensive and complicated, sometimes involving the use of enzymes and occasionally take long periods of time.

SUMMARY OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

According to one aspect of the present invention, there is provided a device configured to mechanically remove a fat phase from at least one adipose tissue, the device comprising a first pressing element and a second pressing element.

According to one embodiment, the device further comprises a fat phase separating element.

According to another embodiment, the fat phase separating element is a sucking element.

According to yet another embodiment, the fat phase separating element is a drainage element.

According to still another embodiment, the device further comprises at least one perforating element.

According to a further embodiment, at least one of the pressing elements is substantially flat.

According to yet a further embodiment, at least one of the pressing elements is substantially cylindrical.

According to still a further embodiment, the first pressing element has a bowl-like structure comprising a base and at least one wall, and the second pressing element has a bowl-like structure comprising a base and at least one wall, wherein the bowl-like second pressing element is configured to be accommodated in a space defined by the base and the at least one wall of the bowl-like first pressing element.

According to an additional embodiment, the device comprising a bowl-like first pressing element and a bowl-like second pressing element, further comprises a pressing and perforating unit comprising a frame enclosing a lattice of a plurality of crossed strips defining a plurality of lattice spaces; the frame and lattice comprising a first surface configured to be in contact with at least one adipose tissue and a second surface; the pressing and perforating unit further comprising at least one perforating member comprising a tip pointing towards the first surface and configured to perforate at least one adipose tissue by extending beyond the first surface, a leg attached to the tip and a resilient connector connecting the tip to a strip; wherein the pressing and perforating unit is configured to be placed on the base of the bowl-like first pressing element.

According to another aspect of the present invention, there is provided a method for preparing a preparation comprising a fat-depleted adipose tissue, the method comprising: mechanically removing a fat phase from at least one adipose tissue.

According to one embodiment, the mechanically removing a fat phase from at least one adipose tissue comprises: homogenizing the at least one adipose tissue to provide a homogenate, and extracting a fat-depleted adipose tissue from the homogenate.

According to another embodiment, the mechanically removing a fat phase from at least one adipose tissue comprises: pressing the at least one adipose tissue.

According to yet another embodiment, the pressing at least one adipose tissue comprises: pressing the at least one adipose tissue between a first pressing element and a second pressing element.

According to still another embodiment, the method further comprises: separating the fat phase from the fat-depleted adipose tissue.

According to a further embodiment, the method further comprises: perforating the at least one adipose tissue.

According to yet a further embodiment, the method further comprises: adding a preparation which is configured to enhance proliferation and differentiation of mesenchymal stem cells.

According to still a further embodiment, the method further comprises: mixing with at least one type of bone tissue.

According to an additional embodiment, the method further comprises: mixing with at least one type of bone substitute.

According to a further aspect of the present invention, there is provided a preparation comprising a fat-depleted adipose tissue, wherein the fat-depleted adipose tissue is prepared by mechanically removing a fat phase from at least one adipose tissue.

According to one embodiment, the preparation further comprises a preparation which is configured to enhance proliferation and differentiation of mesenchymal stem cells.

According to another embodiment, the preparation further comprises at least one type of bone tissue.

According to yet another embodiment, the preparation further comprises at least one type of bone substitute.

BRIEF DESCRIPTION OF THE DRAWINGS

Embodiments are herein described, by way of example only, with reference to the accompanying drawings. With specific reference now to the drawings in detail, it is stressed that the particulars shown are by way of example and for purposes of illustrative discussion of the preferred embodiments, and are presented in the cause of providing what is believed to be the most useful and readily understood description of the principles and conceptual aspects of the embodiments. In this regard, no attempt is made to show structural details in more detail than is necessary for a fundamental understanding, the description taken with the drawings making apparent to those skilled in the art how several forms may be embodied in practice.

In the drawings.

DESCRIPTION OF THE PREFERRED EMBODIMENTS

Figure 1:
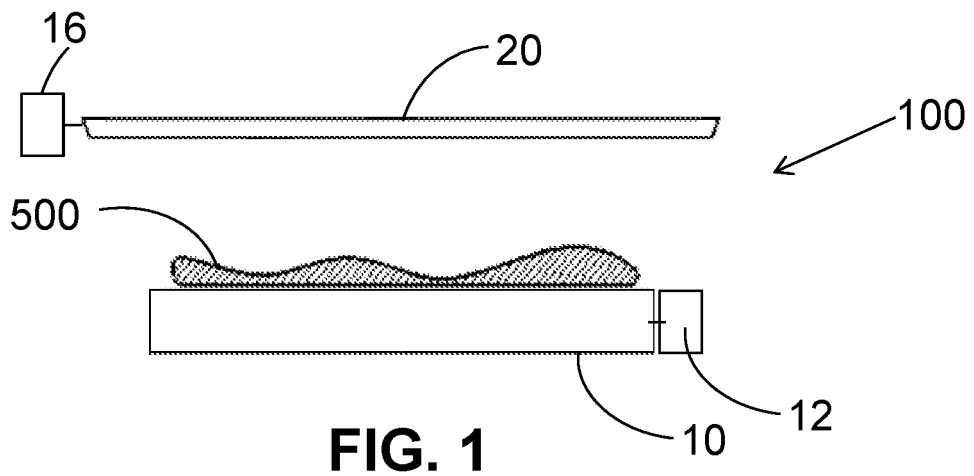
FIG. 1 schematically illustrates, according to an exemplary embodiment, a fat phase removing device, comprising a first pressing element and a second pressing element.

Before explaining at least one embodiment in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting. In discussion of the various figures described herein below, like numbers refer to like parts. The drawings are generally not to scale.

For clarity, non-essential elements were omitted from some of the drawings.

It is an object of the present invention to provide a simple and inexpensive device and method for providing within a short period of time a preparation derived from an adipose tissue which is suitable for transplantation or injection in a patient with a need for soft tissue or bone tissue regeneration.

One aim of the present invention is to provide a device for preparing a preparation comprising a fat-depleted adipose tissue.

Another aim of the present invention is to provide a method for preparing a preparation comprising a fat-depleted adipose tissue.

Yet another aim of the present invention is to provide a preparation comprising a fat-depleted adipose tissue, configured to be transplanted or injected in a patient with a need for soft tissue or bone regeneration.

The term "adipose tissue" as disclosed herein refers to a fat tissue obtained from an animal, the adipose tissue comprising inter alia adipocytes and mesenchymal stem cells.

The term "animal" as disclosed herein refers to any eukaryotic multicellular organism having an adipose tissue, including human being.

The term "patient" as disclosed herein refers to an animal from which an adipose tissue may be provided, and/or with a need for soft tissue or bone regeneration.

The term "fat phase" as disclosed herein refers to a portion of an adipose tissue comprising, according to some embodiments, intact adipose cells, namely adipocytes. According to some other embodiments, the fat phase may further comprise triglycerides. According to some additional embodiments, the fat phase may further comprise cholesteryl ester. According to still additional embodiment, the fat phase may further comprise adipocyte debris.

A "fat-depleted adipose tissue" as disclosed herein refers to an adipose tissue from which at least part of a fat phase was removed by mechanical means. According to some embodiments, a preparation comprising the fat-depleted adipose tissue is configured to be transplanted or injected in a patient with a need for soft tissue regeneration. According to some other embodiments, a preparation comprising the fat-depleted adipose tissue is configured to be transplanted or injected in a patient with a need for bone regeneration. It should be noted though, that any use of a preparation comprising a fat-depleted adipose tissue prepared according to embodiments of the present invention is under the scope of the present invention.

According to one aspect of the present invention, a device for preparing a preparation comprising a fat-depleted adipose tissue, occasionally termed hereinafter as "fat phase removing device", or "the device", is provided.

According to another aspect of the present invention, a method for preparing a preparation comprising a fat-depleted adipose tissue, occasionally termed hereinafter as "the method", is provided.

According to yet another aspect of the present invention, a preparation comprising a fat-depleted adipose tissue, configured to be transplanted or injected in a patient with a need for soft tissue or bone regeneration, occasionally term hereinafter as "the preparation", is provided.

FIG. 1 schematically illustrates, according to an exemplary embodiment, a fat phase removing device 100, comprising a first pressing element 10 and a second pressing element 20. The device 100 is configured to mechanically remove a fat phase from at least one adipose tissue 500. Furthermore, the device 100 is configured to press at least one adipose tissue 500 in between the first pressing element 10 and the second pressing element 20, in a manner that forces out at least part of a fat phase from the at least one adipose tissue 500. Pressing at least one adipose tissue 500 in between the first pressing element 10 and the second pressing element 20 may crush adipose cells, for example large adipose cells, present in the at least one adipose tissue 500. As a result, at least part of a fat phase is forced out from the at least one adipose tissue 500.

According to one embodiment, the first pressing element 10 is stationary, and the second pressing element 20 moves towards the first pressing element, while pressing at least one adipose tissue 500 in between. According to another embodiment, the second pressing element 20 is stationary and the first pressing element 10 moves towards the second pressing element 20, while pressing at least one adipose tissue 500 in between. According to a further embodiment, the first pressing element 10 and the second pressing element 20 both move one towards the other, while pressing at least one adipose tissue 500 in between.

According to one embodiment, the first pressing element 10 is above the second pressing element 20 (not shown). According to another embodiment, the first pressing element 10 is below the second pressing element 20, as illustrated in FIG. 1. According to a further embodiment, the first pressing element 10 is aside the second pressing element 20. According to ant one of the aforementioned embodiments, at least one adipose tissue 500 is placed in between the first pressing element 10 and the second pressing element 20 during the pressing of the at least one adipose tissue 500.

According to some embodiments, the first pressing element 10 and the second pressing element 20 are substantially flat, as illustrated for example in FIG. 1. Thus, a first pressing element 10 is for example a table surface, and a second pressing element 20 is for example weight-like element. It should be noted though that the first pressing element 10 and the second pressing element 20 may have any structure which enables pressing of at least one adipose tissue 500.

According to one embodiment, the first pressing element 10 and/or the second pressing element 20, which moves during the pressing of at least one adipose piece 500, is manually moved. For example but not limited to, the moving pressing element 10 or 20 may be held by a hand of a user and moved towards the other pressing element 20 or 10 during the pressing of at least one adipose tissue 500.

According to another embodiment, the first pressing element 10 and/or the second pressing element 20, which moves during the pressing of at least one adipose piece 500, is moved by a mechanical mechanism, for example but not limited to, a motor, an electrical motor, a manually operated mechanical mechanism, and the like.

According to yet another embodiment, any combination of the ways for moving a pressing element, in case where both the first pressing element 10 and the second pressing element 20 are moving, is under the scope of the present invention. For example, the first pressing element 10 and the second pressing element 20 may be manually moved; the first pressing element 10 and the second pressing element 20 may be moved by a mechanical mechanism; the first pressing element 10 may be manually moved and the second pressing element 20 may be moved by a mechanical mechanism, or vice versa.

According to an additional embodiment, the first pressing element 10 and the second pressing element 20 are configured to apply a controlled pressure on the at least one adipose tissue 500 during pressing. The pressure level affects the amount of fat phase removed from the at least one adipose tissue 500 in one hand, and affects the quality of the obtained fat-depleted adipose tissue on the other hand. Accordingly, a certain minimal pressure level should be applied on the at least one adipose tissue 500 in order to enable removal of fat phase from the at least one adipose tissue. On the other hand, a certain maximal pressure level should be applied on the at least one adipose tissue 500 in order to avoid destruction of the at least one adipose tissue, rendering the obtained fat-depleted adipose tissue useless. Thus, according to this embodiment, the fat phase removing device 100 further comprises a pressure control element configured to control the pressure which is applied on the at least one adipose tissue 500 by the first pressing element 10 and the second pressing element 20.

According to one embodiment, the first pressing element 10 and the second pressing element 20 are configured to come in contact when pressing at least one adipose tissue 500 in between. According to a preferred embodiment, during pressing of the at least one adipose tissue 500, a gap of a certain size is maintained between the first pressing element 10 and the second pressing element 20, for example, in order to avoid over-pressing or crushing of the at least one adipose tissue 500. The size of the gap maintained between the first pressing element 10 and the second pressing element 20, during pressing of at least one adipose tissue 500, is correlated to the size of the at least one adipose tissue 500 being pressed. According to one embodiment, the gap is in the range of substantially 0-500 μm. According to another embodiment, the gap is in the range of substantially 0-300 μm. According to yet another embodiment, the gap is in the size of substantially 150 μm. It should be noted, though, that a gap maintained in any size between the first pressing element 10 and the second pressing element 20 is within the scope of the present invention. Thus, according to this embodiment, the fat phase removing device 100 further comprises a distance controlling element 16, configured to control the distance of movement of the first pressing element 10 and/or the second pressing element 20 towards each other, in order to maintain a gap of a predetermined size between the first pressing element 10 and the second pressing element 20.

According to another embodiment, the first pressing element 10 and/or the second pressing element 20, which moves during the pressing of at least one adipose tissue 500, comprises at least one weight-like element having a known weight value. Thus, according to an exemplary embodiment, the first pressing element 10 is stationary. At least one adipose tissue 500 is placed on the first pressing element 10, and the second pressing element 20 comprises at least one weight-like element, which presses the at least one adipose tissue 500 from above. According to this embodiment, controlling the pressure applied on the at least one adipose tissue 500 is achieved by using at least one weight-like element with a desired weight value.

According to yet another embodiment, the first pressing element 10 and/or the second pressing element 20, which moves during the pressing of at least one adipose tissue 500, is configured to move in a certain velocity. The velocity of the movement of a moving pressing element affects the amount of fat phase removed from the at least one adipose tissue 500 in one hand, and affects the quality of the obtained fat-depleted adipose tissue on the other hand. Thus, according to this embodiment, the fat phase removing device 100 further comprises a velocity control element configured to control the velocity in which a moving pressing element moves when pressing at least one adipose tissue 500.

According to still another embodiment, the fat phase removing device 100 is configured to press the at least one adipose tissue 500 for a certain period of time. The period of time during which the at least one adipose tissue 500 is pressed affects the amount of fat phase removed from the at least one adipose tissue 500 in one hand, and affects the quality of the obtained fat-depleted adipose tissue on the other hand. Thus, according to this embodiment, the fat phase removing device 100 further comprises a timer configured to control the period of time during which the at least one adipose tissue 500 is pressed.

According to an additional embodiment, the fat phase removing device 100 is configured to press the at least one adipose tissue 500 under a controlled temperature. The temperature under which the at least one adipose tissue 500 is pressed affects the amount of fat phase removed from the at least one adipose tissue 500 in one hand, and affects the quality of the obtained fat-depleted adipose tissue on the other hand. For example, increasing the temperature renders fatty material in the at least one adipose tissue 500 more fluid and less solid, thus increasing the amount of fat phase removed from the at least one adipose tissue 500 during pressing. On the other hand, increasing the temperature too much may threaten the viability of cells present in the fat-depleted adipose tissue. According to some exemplary embodiments, the fat phase removing device 100 is configured to press the at least one adipose tissue 500 under, for example but not limited to, ambient temperature, a temperature in the range of substantially 18-28° C., and preferably a temperature in the range of substantially 37-42° C. Thus, according to this embodiment, the fat phase removing device 100 further comprises a temperature control element 12 configured to control the temperature under which the at least one adipose tissue 500 is pressed.

According to some embodiments, the fat phase removing device 100 further comprises a fat phase separating element. According to one embodiment, the fat phase separating element is separated from the first pressing element 10 and/or the second pressing element 20. According to another embodiment, the fat phase separating element is attached to the first pressing element 10 and/or the second pressing element 20. According to yet another embodiment, the fat phase separating element is part of the first pressing element 10 and/or the second pressing element 20.

According to some embodiments, the fat phase separating element is configured to separate the fat phase from the fat-depleted adipose tissue during the pressing of the at least one adipose tissue 500 with the fat phase removing device 100. According to some other embodiments, the fat phase separating element is configured to separate the fat phase from the fat-depleted adipose tissue after the pressing of the at least one adipose tissue 500 with the fat phase removing device 100.

According to one embodiment, the fat phase separating element is a sucking element configured to suck a fat phase, thus separating the fat phase from the fat-depleted adipose tissue. Examples of a sucking element include, but not limited to, a syringe-like element, an aspirator-like element, and a catheter fluidically connected to a vacuum pump.

According to another embodiment, the fat phase separating element is a drainage element, separating the fat phase from the fat-free adipose tissue by draining the fat phase away. Examples of a drainage element include, but not limited to, a drainage slot on a surface of a pressing element 10 and/or 20 configured to allow flow of a fat phase away from the pressed at least one adipose tissue 500 during or after pressing. According to one embodiment, the first pressing element 10 comprises a drainage element. According to another embodiment, the second pressing element 20 comprises a drainage element. According to yet another embodiment, both the first pressing element 10 and the second pressing element 20 comprise a drainage element.

Figure 2:
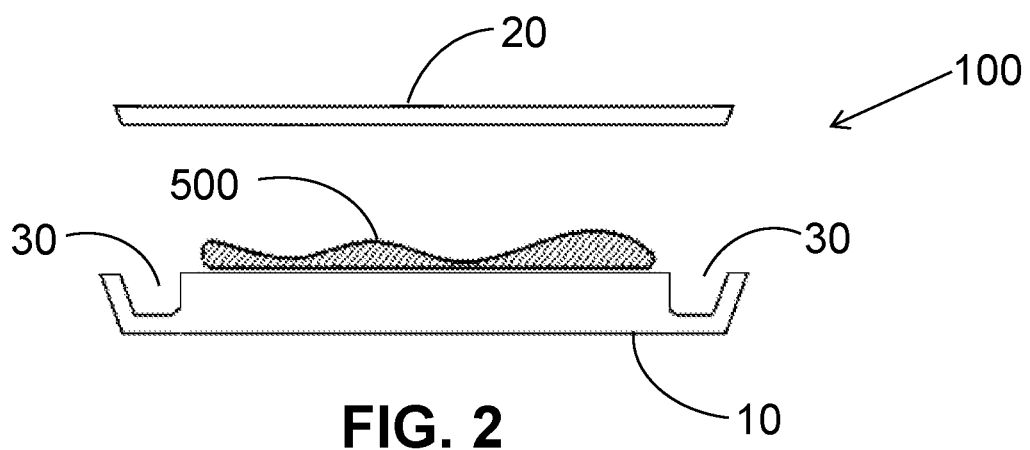
FIG. 2 schematically illustrates, according to an exemplary embodiment, a cross-section view of a fat phase removing device, further comprising a drainage element.

FIG. 2 schematically illustrates, according to an exemplary embodiment, a cross-section view of a fat phase removing device 100, further comprising a drainage element 30. According to the exemplary embodiment illustrated in FIG. 2, the drainage element 30 is a drainage slot in the periphery of the first pressing element 10.

According to some embodiments, the fat phase removing device 100 further comprises at least one perforating element. The at least one perforating element is configured to perforate or incise the at least one adipose tissue 500 in a manner that facilitates exit of a fat phase from the at least one adipose tissue 500 during pressing of the at least one adipose tissue 500.

According to some embodiments, the perforating element is separated from the first pressing element 10 and/or the second pressing element 20. Any perforating element known in the art, which is configured to perforate or incise at least one adipose tissue 500 is under the scope of the present invention, for example but not limited to, a needle, a scalpel, tweezers, an element comprising a plurality of tooth-like structures resembling a comb or a brush, and the like.

According to some other embodiments, the at least one perforating element is attached to the first pressing element 10 and/or the second pressing element 20 in a manner that allows perforation or incision of the at least one adipose tissue 500 during pressing with the fat phase removing device 100. It should be noted in this context that the term "attached" is defined as physically attached, for example by gluing or welding, or as being part of the fat phase removing device 100, for example created during casting of a pressing element 10 and/or 20 made of metal or plastic. An example for illustrative purposes only of a perforating element attached to the first pressing element 10 and/or the second pressing element 20 is an at least one tooth-like structure attached to the surface of the first pressing element 10 and/or the second pressing element 20.

Figure 3:
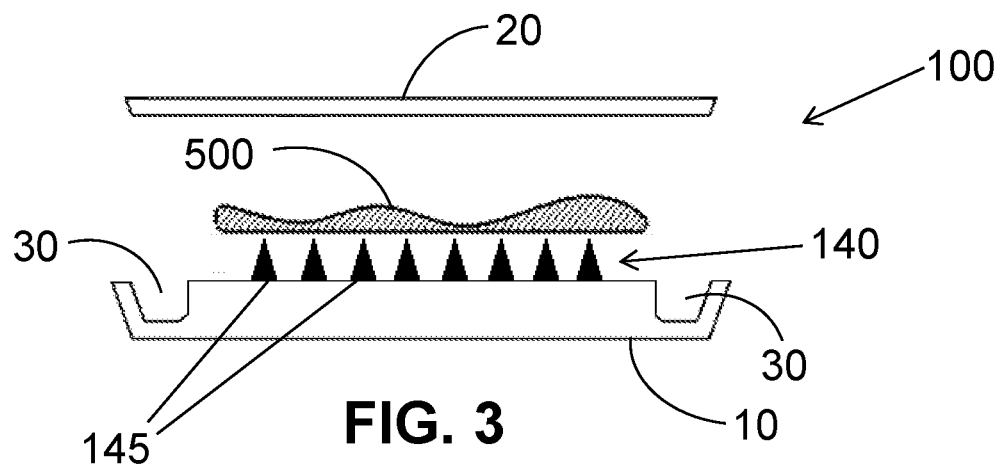
FIG. 3 schematically illustrates, according to an exemplary embodiment, a cross-section view of a fat phase removing device further comprising a perforating element attached to the first pressing element.

FIG. 3 schematically illustrates, according to an exemplary embodiment, a cross-section view of a fat phase removing device 100 further comprising a perforating element 140 attached to the first pressing element 10. The perforating element 140 may be of any type as described above. According to the exemplary embodiment illustrated in FIG. 3, the perforating element 140 comprises at least one tooth-like structure 145. During the pressing of the at least one adipose tissue 500 between the first pressing element 10 and the second pressing element 20, the perforating element 140 which is attached to the surface of the first pressing element 10 is configured to perforate the at least one adipose tissue 500 and facilitate exit of a fat phase from the at least one adipose tissue 500 during pressing.

Figure 4:
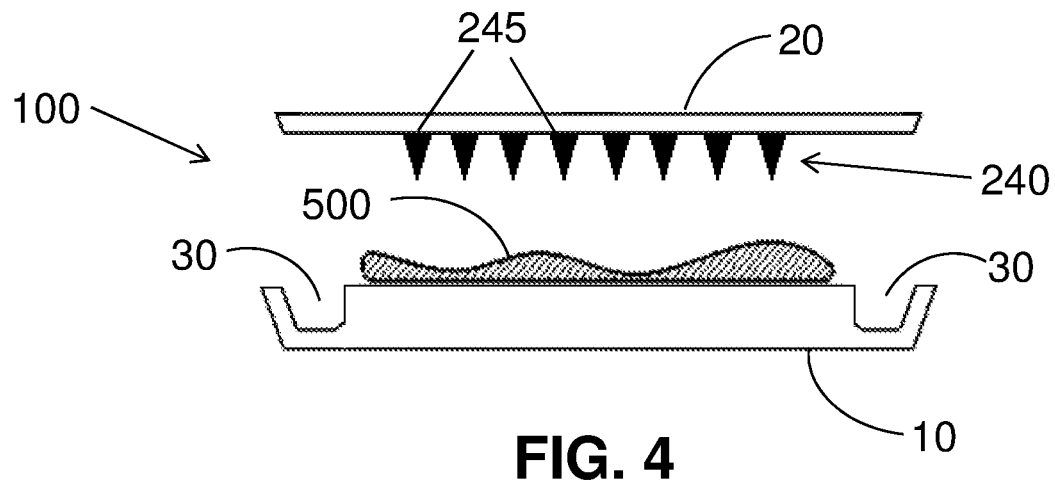
FIG. 4 schematically illustrates, according to an exemplary embodiment, a cross section view of a fat phase removing device further comprising a perforating element attached to the second pressing element.

FIG. 4 schematically illustrates, according to an exemplary embodiment, a cross section view of a fat phase removing device 100 further comprising a perforating element 240 attached to the second pressing element 20. According to the exemplary embodiment illustrated in FIG. 4, the perforating element 240 comprises at least one tooth-like structure 245. During the pressing of the at least one adipose tissue 500 between the first pressing element 10 and the second pressing element 20, the perforating element 240 which is attached to the surface of the second pressing element 20 is configured to perforate the at least one adipose tissue 500 and facilitate exit of a fat phase from the at least one adipose tissue 500 during pressing.

Figure 5:
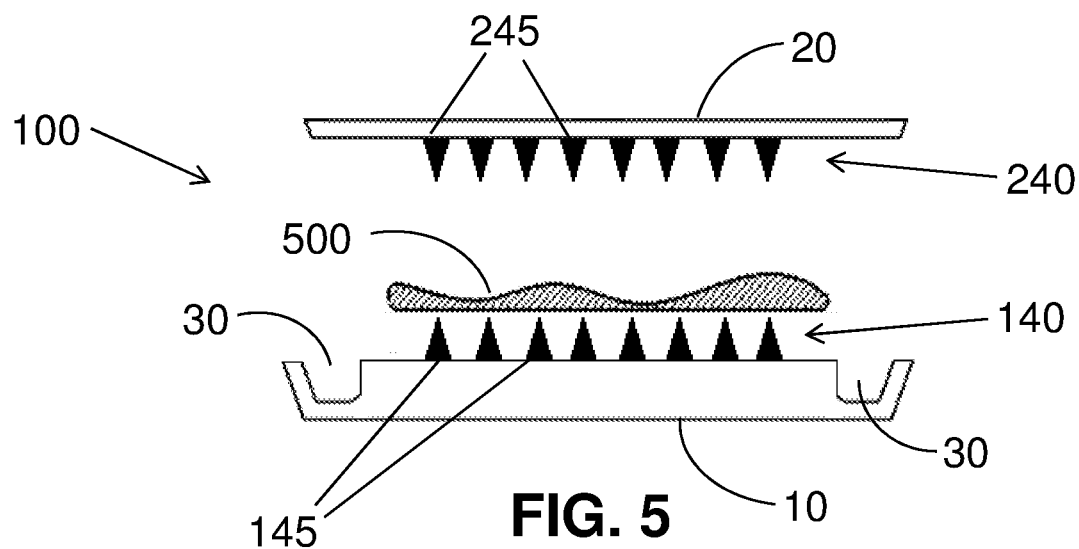
FIG. 5 schematically illustrates, according to an exemplary embodiment, a cross section view of a fat phase removing device further comprising a perforating element comprising at least one tooth-like structure, attached to the first pressing element, and a perforating element comprising at least one tooth-like structure, attached to the second pressing element.

FIG. 5 schematically illustrates, according to an exemplary embodiment, a cross section view of a fat phase removing device 100 further comprising a perforating element 140 comprising at least one tooth-like structure 145, attached to the first pressing element 10, and a perforating element 240 comprising at least one tooth-like structure 245, attached to the second pressing element 20. During the pressing of the at least one adipose tissue 500 between the first pressing element 10 and the second pressing element 20, both perforating elements 140 and 240 are configured to perforate the at least one adipose tissue 500 and facilitate exit of a fat phase from the at least one adipose tissue 500 during pressing.

According to the embodiments illustrated in FIGS. 1-5, the first pressing element 10 and the second pressing element 20 are substantially flat. According to some other embodiments, at least one of the pressing elements is substantially cylindrical, namely either the first pressing element 10 and/or the second pressing element are substantially cylindrical. According to some further embodiments, at least one of the pressing elements is substantially flat. According to some additional embodiments, at least one of the pressing elements is substantially cylindrical. Nevertheless, it should be emphasized again that any structure of the first pressing element 10 and the second pressing element 20, which is configured to enable pressing of at least one adipose tissue 500, is under the scope of the present invention.

Figure 6:
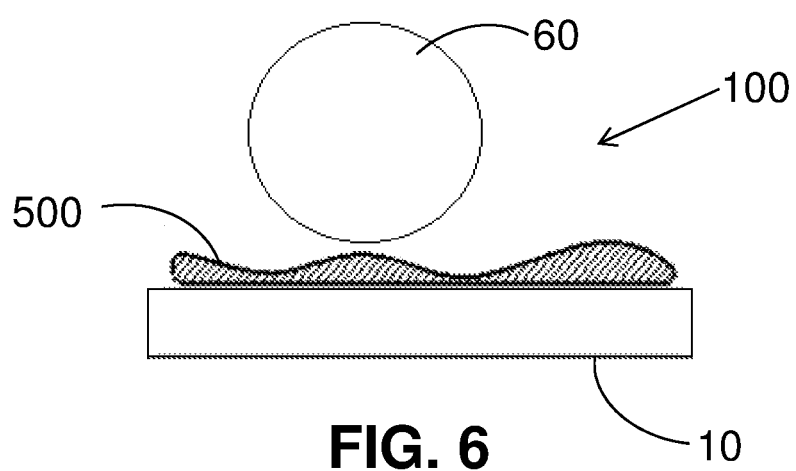
FIG. 6 schematically illustrates, according to an exemplary embodiment, a cross-section view of a fat phase removing device comprising a substantially flat first pressing element and a substantially cylindrical second pressing element.

FIG. 6 schematically illustrates, according to an exemplary embodiment, a cross-section view of a fat phase removing device 100 comprising a substantially flat first pressing element 10 and a substantially cylindrical second pressing element 60, configured to press at least one adipose tissue 500 in between the substantially flat first pressing element 10 and the substantially cylindrical second pressing element 60, in a manner that forces out at least part of a fat phase from the at least one adipose tissue 500. The substantially cylindrical second pressing element 60 is configured to roll over the at least one adipose tissue 500 while pressing the at least one adipose tissue 500.

Figure 7:
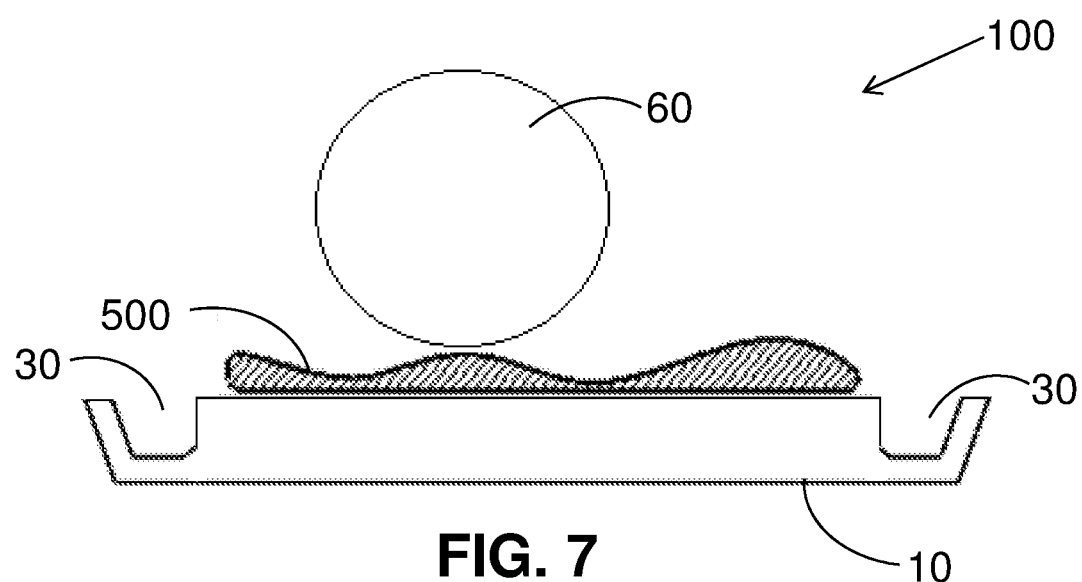
FIG. 7 schematically illustrates, according to an exemplary embodiment, a cross-section view of a fat phase removing device comprising a substantially flat first pressing element and a substantially cylindrical second pressing element, wherein the substantially flat first pressing element further comprises a drainage element.

FIG. 7 schematically illustrates, according to an exemplary embodiment, a cross-section view of a fat phase removing device 100 comprising a substantially flat first pressing element 10 and a substantially cylindrical second pressing element 60, wherein the substantially flat first pressing element 10 further comprises a drainage element 30. According to the exemplary embodiment illustrated in FIG. 7, the drainage element 30 is a drainage slot in the periphery of the substantially flat first pressing element 10.

Figure 8:
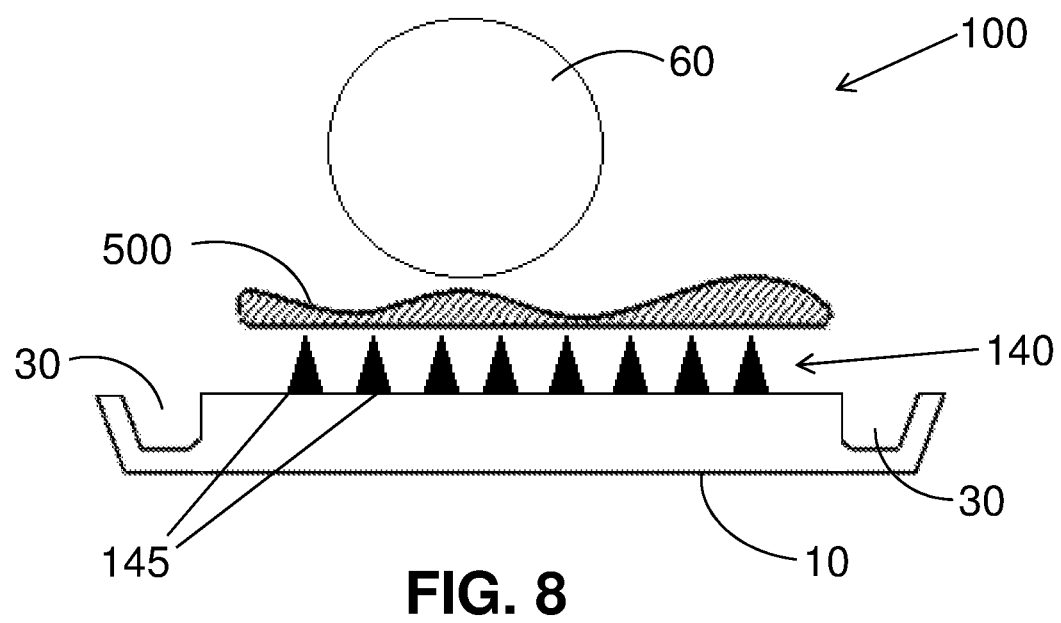
FIG. 8 schematically illustrates, according to an exemplary embodiment, a cross-section view of a fat phase removing device comprising a substantially flat first pressing element and a substantially cylindrical second pressing element, wherein the substantially flat first pressing element further comprises a drainage element and a perforating element, comprising at least one tooth-like structure, attached to the substantially flat first pressing element.

FIG. 8 schematically illustrates, according to an exemplary embodiment, a cross-section view of a fat phase removing device 100 comprising a substantially flat first pressing element 10 and a substantially cylindrical second pressing element 60, wherein the substantially flat first pressing element 10 further comprises a drainage element 30 and a perforating element 140, comprising at least one tooth-like structure 145, attached to the substantially flat first pressing element 10.

Figure 9:
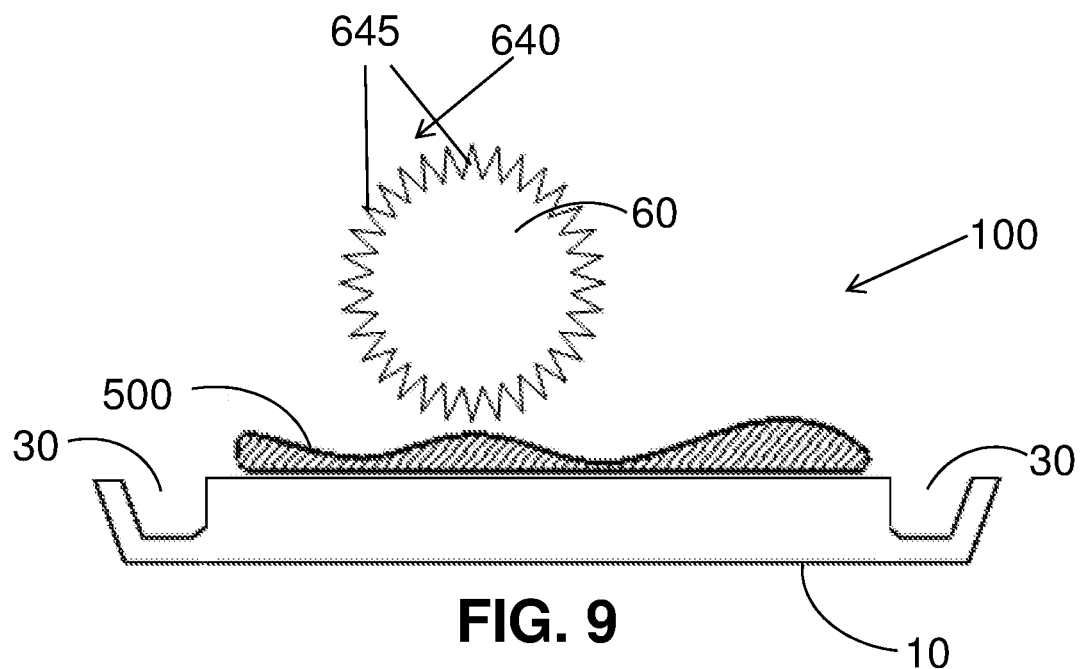
FIG. 9 schematically illustrates, according to an exemplary embodiment, a cross-section view of a fat phase removing device comprising a substantially flat first pressing element and a substantially cylindrical second pressing element, wherein the substantially flat first pressing element further comprises a drainage element, and the substantially cylindrical second pressing element further comprises a perforating element.

FIG. 9 schematically illustrates, according to an exemplary embodiment, a cross-section view of a fat phase removing device 100 comprising a substantially flat first pressing element 10 and a substantially cylindrical second pressing element 60, wherein the substantially flat first pressing element 10 further comprises a drainage element 30, and the substantially cylindrical second pressing element 60 further comprises a perforating element 640. As described above, the perforating element 640 may be of any type. According to the exemplary embodiment illustrated in FIG. 9, the perforating element 640 comprises at least one tooth-like structure 645.

Figure 10:
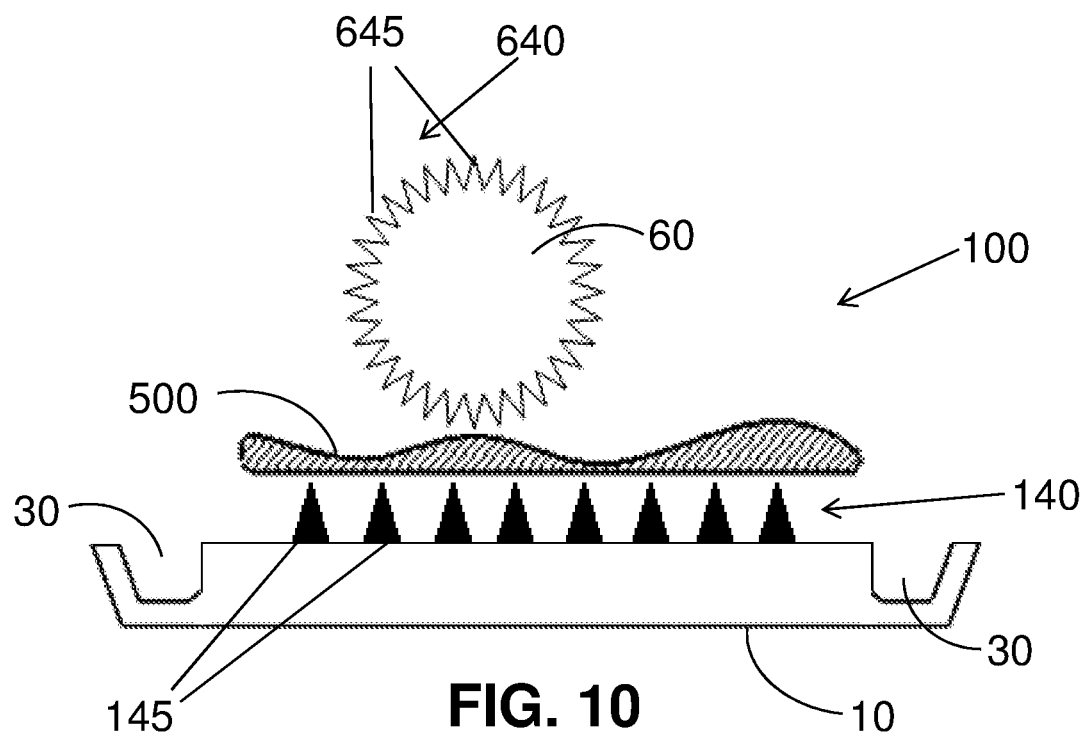
FIG. 10 schematically illustrates, according to an exemplary embodiment, a cross-section view of a fat phase removing device comprising a substantially flat first pressing element and a substantially cylindrical second pressing element, wherein the substantially flat first pressing element further comprises a drainage element, and a perforating element comprising at least one tooth-like structure, and the substantially cylindrical second pressing element further comprises a perforating element comprising at least one tooth-like structure.

FIG. 10 schematically illustrates, according to an exemplary embodiment, a cross-section view of a fat phase removing device 100 comprising a substantially flat first pressing element 10 and a substantially cylindrical second pressing element 60, wherein the substantially flat first pressing element 10 further comprises a drainage element 30, and a perforating element 140 comprising at least one tooth-like structure 145, and the substantially cylindrical second pressing element 60 further comprises a perforating element 640 comprising at least one tooth-like structure 645.

According to the embodiments illustrated in FIG. 6-10, one of the two pressing elements is substantially flat and the other pressing element is substantially cylindrical. Several embodiments regarding the movement of the pressing elements—one relative to the other, are as follows: According to one embodiment, the substantially flat pressing element is configured to be stationary and the substantially cylindrical pressing element is configured to roll along the surface of the substantially flat pressing element during the pressing of the at least one adipose tissue 500. According to another embodiment, the substantially cylindrical pressing element is configured to be stationary and roll along the surface of the substantially flat pressing element, which moves in a manner that allows rolling of the substantially cylindrical pressing element along the surface of the substantially flat pressing element, during the pressing of the at least one adipose tissue 500. According to yet another embodiment, both the substantially cylindrical pressing element and the substantially flat pressing element are configured to move in a manner that allows rolling of the substantially cylindrical pressing element along the surface of the substantially flat pressing element, during the pressing of the at least one adipose tissue 500.

According to some additional embodiments, both the first pressing element and the second pressing element are substantially cylindrical. According to these embodiments, both substantially cylindrical pressing elements are configured to roll one relative to the other in a manner that presses the at least one adipose tissue 500.

Figure 11:
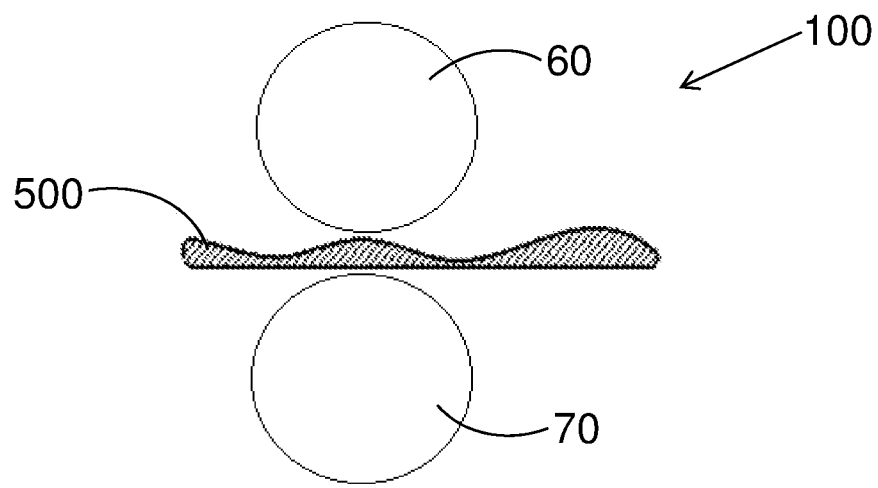
FIG. 11 schematically illustrates, according to an exemplary embodiment, a cross-section view of a fat phase removing device comprising a substantially cylindrical first pressing element and a substantially cylindrical second pressing element.

FIG. 11 schematically illustrates, according to an exemplary embodiment, a cross-section view of a fat phase removing device 100 comprising a substantially cylindrical first pressing element 70 and a substantially cylindrical second pressing element 60, both configured to press at least one adipose tissue 500 in between.

Figure 12:
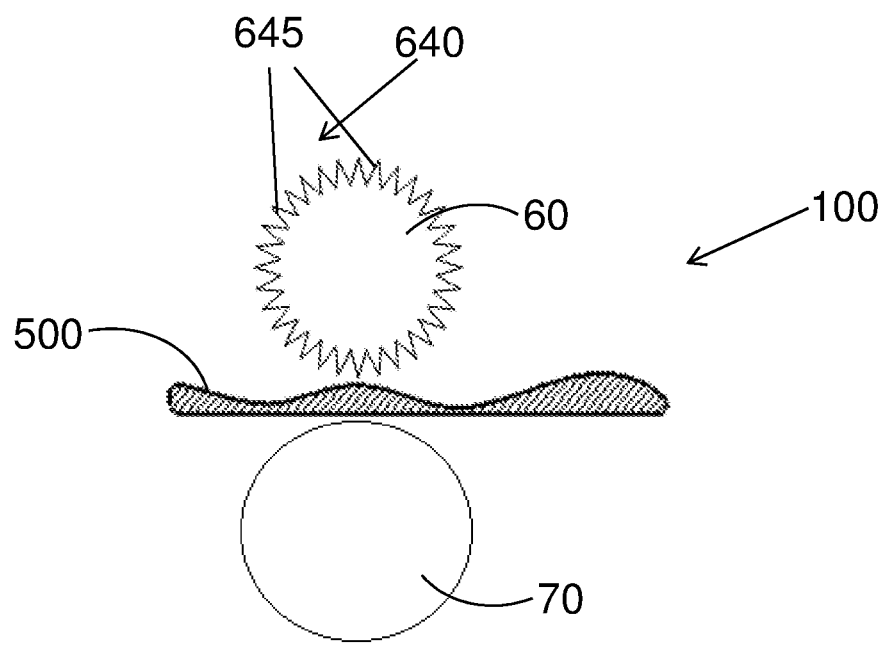
FIG. 12 schematically illustrates, according to an exemplary embodiment, a cross-section view of a fat phase removing device comprising a substantially cylindrical first pressing element and a substantially cylindrical second pressing element, wherein the substantially cylindrical second pressing element further comprises a perforating element comprising at least one tooth-like structure.

FIG. 12 schematically illustrates, according to an exemplary embodiment, a cross-section view of a fat phase removing device 100 comprising a substantially cylindrical first pressing element 70 and a substantially cylindrical second pressing element 60, wherein the substantially cylindrical second pressing element 60 further comprises a perforating element 640 comprising at least one tooth-like structure 645.

Figure 13:
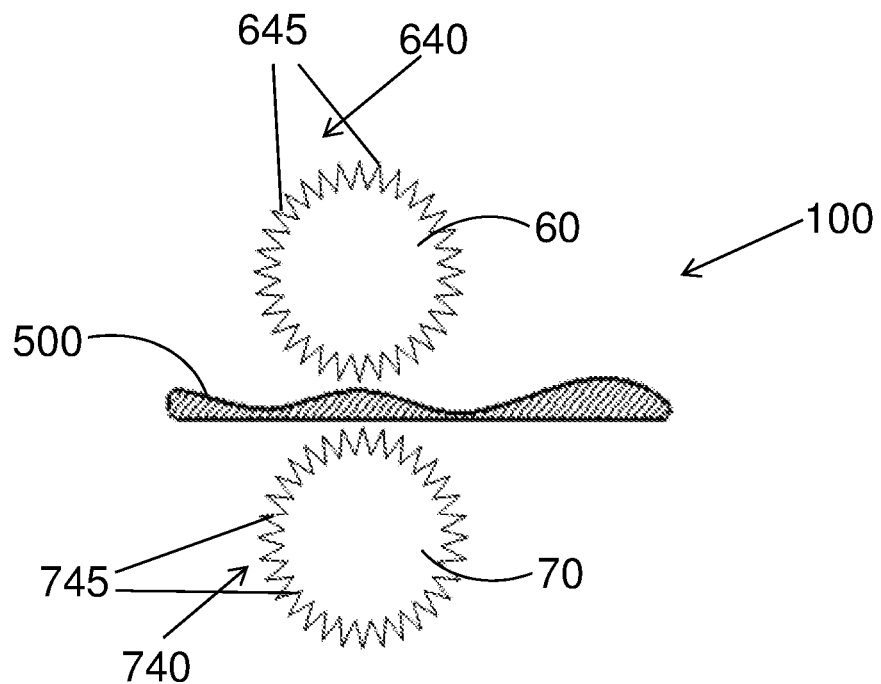
FIG. 13 schematically illustrates, according to an exemplary embodiment, a cross-section view of a fat phase removing device comprising a substantially cylindrical first pressing element and a substantially cylindrical second pressing element, wherein the substantially cylindrical first pressing element further comprises a perforating element comprising at least one tooth-like structure, and the substantially cylindrical second pressing element further comprises a perforating element comprising at least one tooth-like structure.

FIG. 13 schematically illustrates, according to an exemplary embodiment, a cross-section view of a fat phase removing device 100 comprising a substantially cylindrical first pressing element 70 and a substantially cylindrical second pressing element 60, wherein the substantially cylindrical first pressing element 70 further comprises a perforating element 740 comprising at least one tooth-like structure 745, and the substantially cylindrical second pressing element 60 further comprises a perforating element 640 comprising at least one tooth-like structure 645.

Figure 14:
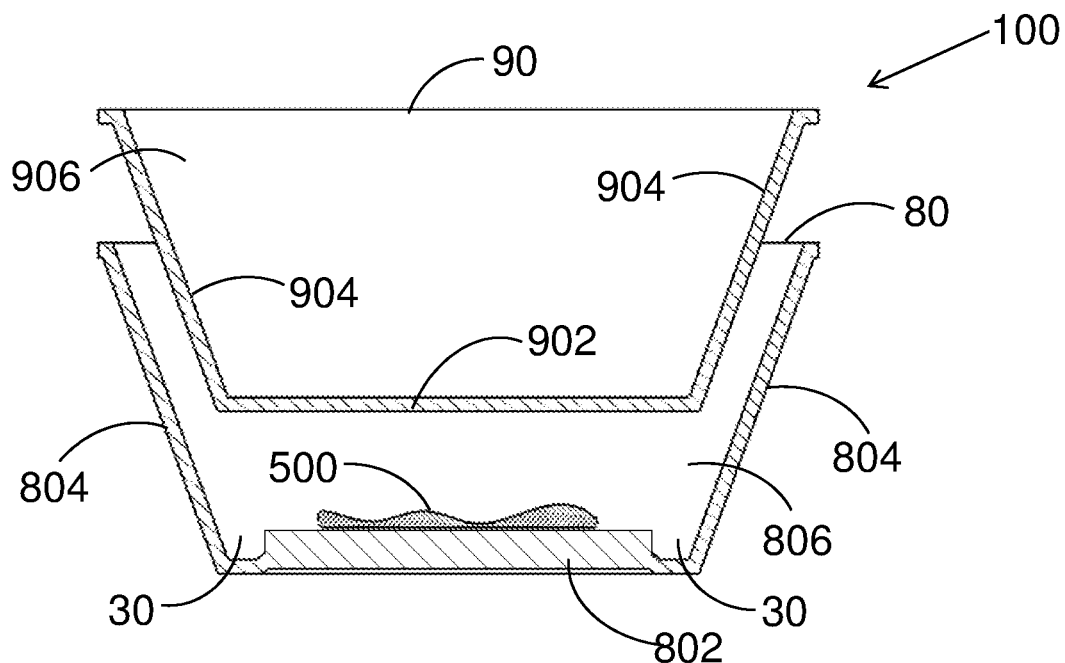
FIG. 14 schematically illustrates, according to an exemplary embodiment, a cross-section view of a fat phase removing device comprising a bowl-like first pressing element and a bowl-like second pressing element.

FIG. 14 schematically illustrates, according to an exemplary embodiment, a cross-section view of a fat phase removing device 100 comprising a bowl-like first pressing element 80 and a bowl-like second pressing element 90.

The bowl-like first pressing element 80 comprises a base 802 configured to allow the placement of at least one adipose tissue 500 on the base 802. The base may have any structure and configuration. According to the preferred exemplary embodiment illustrated in FIG. 14, the base 802 of the bowl-like first pressing element 80 is flat. The bowl-like first pressing element further comprises at least one wall 804, when the number of walls 804 depends on the structure of the base 802. In embodiments according to which the base 802 is circular, there is one wall 804 extending from the perimeter of the circular base 804; whereas in embodiments according to which the base 802 is quadrangular, there are four walls 804, when each wall 804 extends from an edge of the quadrangular base 802. The base 802 and the at least one wall 804 define a space 806. According to some embodiments, the bowl-like first pressing element 80 further comprises a drainage element 30.

The bowl-like second pressing element 90 comprises a base 902 and at least one wall 904, which both define a space 906. The bowl-like second pressing element is configured to be accommodated in the space 806 of the bowl-like first pressing element 80. Thus, any structure and configuration of the bowl-like second pressing element 90, inter alia in terms of the structure of the base 902 and at least one wall 904, which allow accommodation of the bowl-like second pressing element 90 in the space 806 of the bowl-like first pressing element 80, is under the scope of the present invention.

Figure 15:
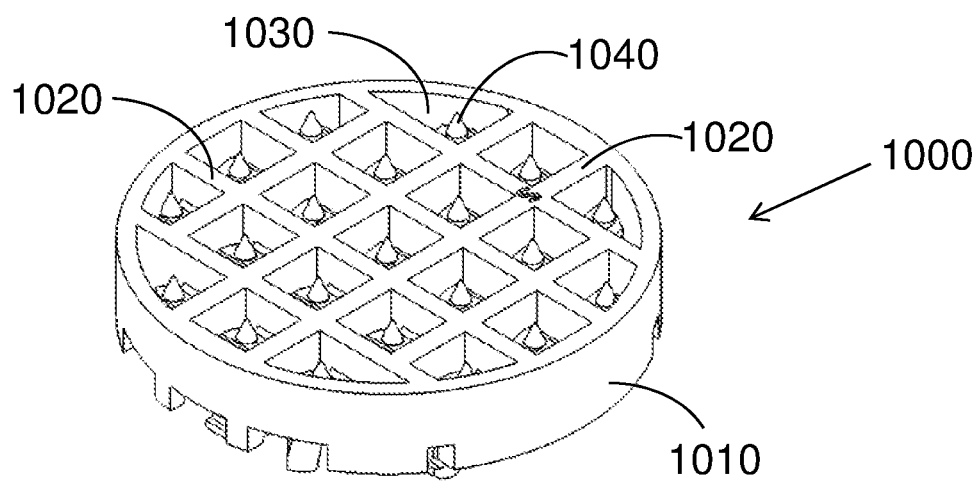
FIG. 15 schematically illustrates, according to an exemplary embodiment, a perspective view of a pressing and perforating unit, configured to press and perforate at least one adipose tissue.

FIG. 15 schematically illustrates, according to an exemplary embodiment, a perspective view of a pressing and perforating unit 1000, configured to press and perforate at least one adipose tissue 500. According to some embodiment, the pressing and perforating unit is configured to perforate and press at least one adipose tissue independently. According to a preferred embodiment, the pressing and perforating unit 1000 is configured to perforate and press at least one adipose tissue 500 in combination with a fat phase removing device 100. According to one embodiment, illustrated in FIG. 15, the pressing and perforating unit 1000 comprises a frame 1010 enclosing a lattice of a plurality of crossed strips 1020 defining a plurality of lattice spaces 1030, and at least one perforating member 1040 configured to extend from a lattice space 1030. According to some embodiments, the pressing and perforating unit 1000 may be in a relaxed state. According to some other embodiments, the pressing and perforating unit 1000 may be in a pressed state.

Figure 16:
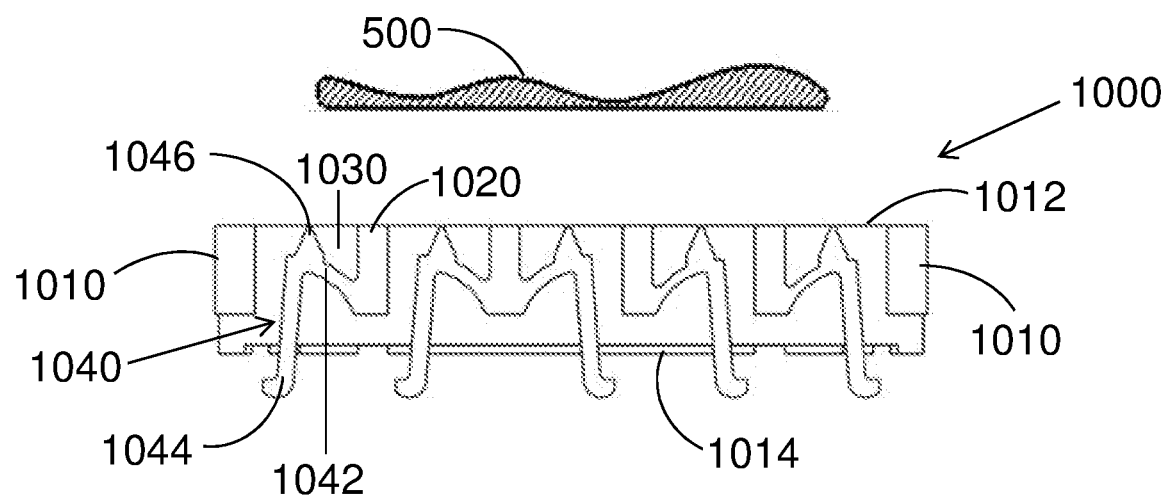
FIG. 16 schematically illustrates, according to an exemplary embodiment, a cross-section view of a pressing and perforating unit, in a relaxed state.

FIG. 16 schematically illustrates, according to an exemplary embodiment, a cross-section view of a pressing and perforating unit 1000, in a relaxed state. The frame 1010 and lattice of a plurality of crossed strips 1020 comprise a first surface 1012 and a second surface 1014. The first surface 1012 is configured to be in contact with at least one adipose tissue 500. The at least one perforating member 1040 comprises a tip 1046 pointing towards the first surface 1012 and configured to perforate at least one adipose tissue 500. The at least one perforating member further comprises a leg 1044 attached to the tip 1046, and a resilient connector 1042 connecting the tip 1046 to a strip 1020.

According to some embodiments, the tip 1046 of the at least one perforating member 1040 has an size and shape which are allow perforation of the at least one adipose tissue 500. According to one embodiment, the tip 1046 is sharp as illustrated for example in FIG. 16. According to another embodiment, the width of the tip 1046 is substantially 1 mm. According to yet another embodiment, the length of the tip is in the range of substantially 0.5-2 mm.

At a relaxed state, as illustrated in FIG. 16, according to a preferred embodiment, a tip 1046 of the at least one perforating member 1040 is positioned at the level of the first surface 1012. According to another embodiment, the tip 1046 extends beyond the first surface 1012 (not shown), and according to yet another embodiment, the tip 1046 is positioned below the first surface 1012. Furthermore, at the relaxed state, according to a preferred embodiment, the leg 1044 extends outwards of the second surface 1014.

Figure 17:
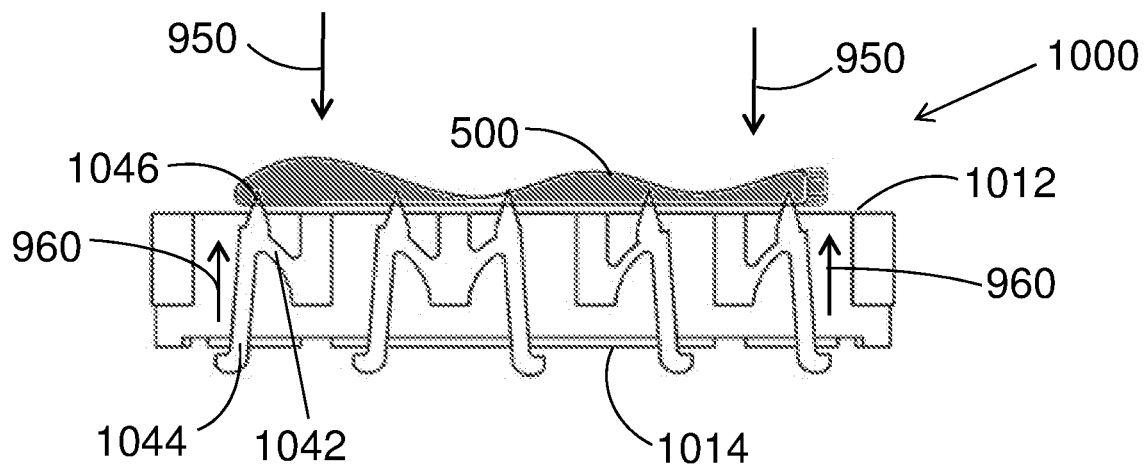
FIG. 17 schematically illustrates according to an exemplary embodiment, a cross-section view of a pressing and perforating unit, in a pressed state.

FIG. 17 schematically illustrates according to an exemplary embodiment, a cross-section view of a pressing and perforating unit 1000, in a pressed state. According to some embodiments, the pressing and perforating unit 1000 is configured to be pressed towards the second surface 1014, as indicated with arrows 950, when the legs 1044 of the at least one perforating member 1040 are placed on a surface (not shown). As a result, due to the contradictory force exerted by the surface on the legs 1044, and the resiliency of the resilient connector 1042, the tips 1046 of the at least one perforating member 1040 are pushed towards the first surface 1012, as indicated with arrows 960, causing the tips 1046 to extend beyond the first surface 1012. If at least one adipose tissue 500 is in contact with the first surface 1012, the tips 1046 perforate the at least one adipose tissue 500 and allow exit of a fat phase from the at least one adipose tissue 500 during the pressing. When the pressure in direction 950 is relieved, due to the resiliency of the resilient connector 1042 the at least one perforating member 1040 returns to the relaxed state, as illustrated in FIG. 16.

Figure 18:
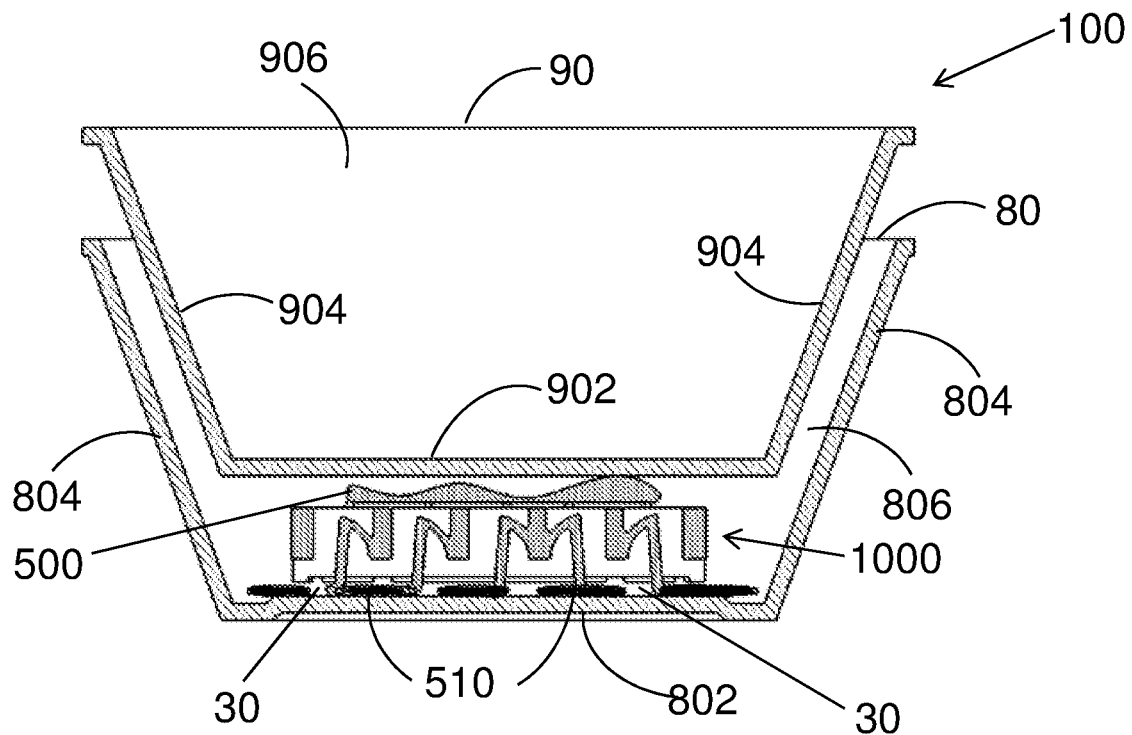
FIG. 18 schematically illustrates, according to an exemplary embodiment, a cross-section view of a fat phase removing device comprising a bowl-like first pressing element and a bowl-like second pressing element, in combination with a pressing and perforating unit.

FIG. 18 schematically illustrates, according to an exemplary embodiment, a cross-section view of a fat phase removing device 100 comprising a bowl-like first pressing element 80 and a bowl-like second pressing element 90, in combination with a pressing and perforating unit 1000. The pressing and perforating unit 1000 stands on the base 802 of the bowl-like first pressing element 80, and at least one adipose tissue 500 is in contact with the first surface 1012 of the pressing and perforating unit 1000. When the at least one adipose tissue 500 is pressed between the first surface 1012 of the pressing and perforating unit 1000 and the base 902 of the bowl-like second pressing element 90, the at least one perforating member 1040 are pushed towards the first surface 1012, and the tips 1046 perforate the at least one adipose tissue 500, as described above. As a result of the pressing and perforation of the at least one adipose tissue 500, fat phase 510 exits the adipose tissue 500 and is collected on the base 802 of the bowl-like first pressing element 80, under the pressing and perforating unit 1000. Thus, the difference in height between the first surface 1012 of the pressing and perforating unit 1000 and the base 802 of the bowl-like first pressing element 80 serves as a drainage element in which the fat phase 510 is collected.

According to some embodiments, a pressure exerting device is provided. According to one general embodiment, the pressure exerting device comprises a body, a holder configured to hold a fat phase removing device 100, and a pushing press configured to provide pressure to the fat phase removing device 100 for pressing at least one adipose tissue. Furthermore, according to some additional embodiments, the pressure exerting device further comprises control elements as described above, for example but not limited to—a pressure control element, a velocity control element, a timer, and a temperature control element.

It should be noted that the embodiments of the pressure exerting device disclosed herein should be understood as exemplary embodiments given for demonstration purposes only, and that any pressure exerting device which is configured to perform the functions disclosed herein is under the scope of the present invention.

Figure 19:
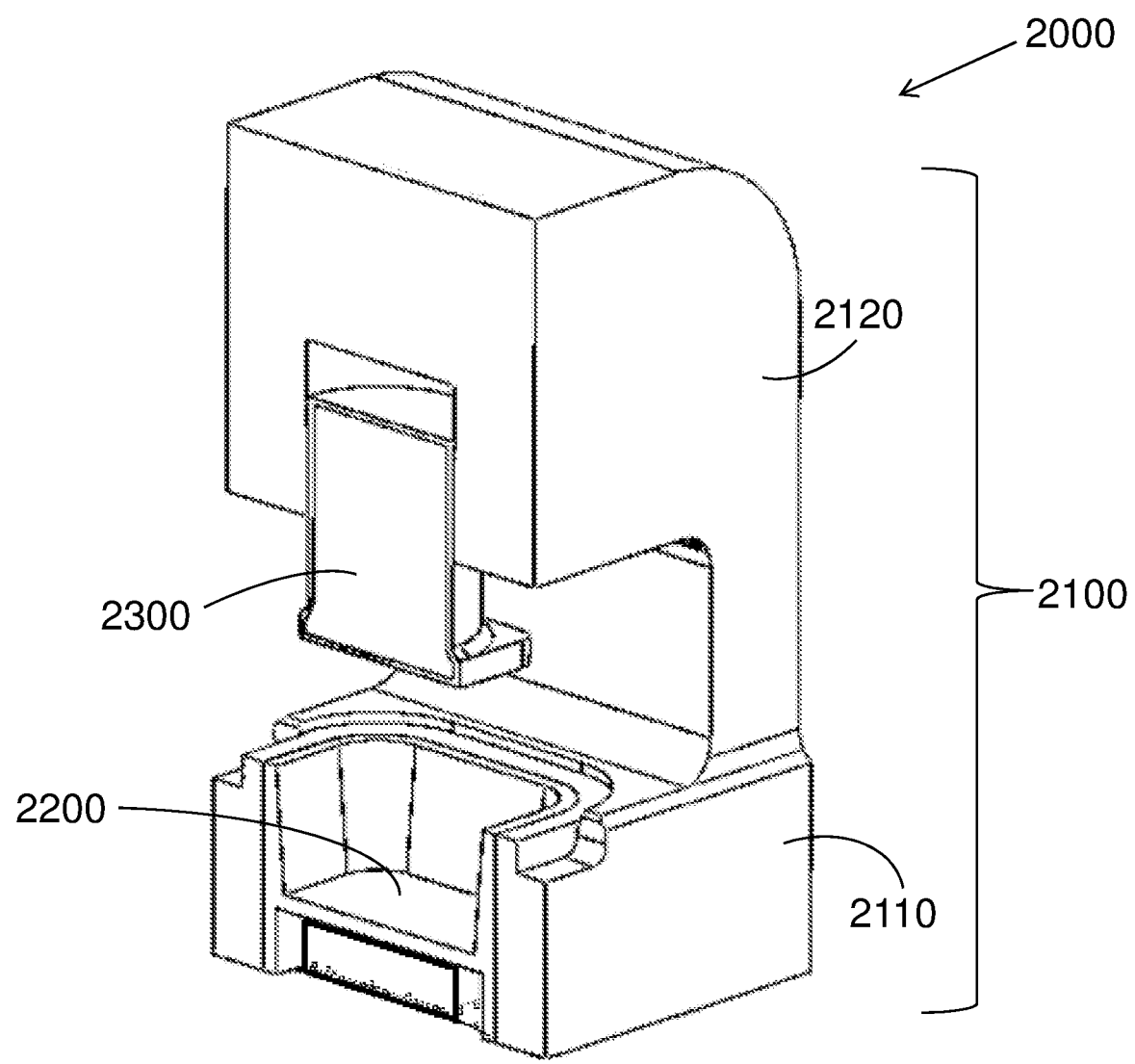
FIG. 19 schematically illustrates, according to an exemplary embodiment, a perspective view of a pressure exerting device.

FIG. 19 schematically illustrates, according to an exemplary embodiment, a perspective view of a pressure exerting device 2000. According to one embodiment, the pressure exerting device 2000, illustrated in FIG. 19, is configured to provide pressure to a fat phase removing device 100 comprising a bowl-like first pressing element 80 and a bowl-like second pressing element 90, as illustrated for example in FIG. 14. According to another embodiment, the pressure exerting device 2000, illustrated in FIG. 19, is configured to provide a pressure to a fat phase removing device 100 comprising a bowl-like first pressing element 80 and a bowl-like second pressing element 90, in combination with a pressing and perforating unit 1000, as illustrated for example in FIG. 18.

According to some embodiments, the pressure exerting device 2000, illustrated in FIG. 19, comprises a body 2100 having a first part 2110 and a second part 2120, a fat phase removing device holder 2200 attached to the first part 2110 of the body 2100, and a pushing press 2300 attached to second part 2120 of the body 2100. According to one embodiment, the fat phase removing device holder 2200 is configured to hold a fat phase removing device 100 comprising a bowl-like first pressing element 80 and a bowl-like second pressing element 90. According to another embodiment, the fat phase removing device holder 2200 is configured to hold a fat phase removing device 100 comprising a bowl-like first pressing element 80 and a bowl-like second pressing element 90, in combination with a pressing and perforating unit 1000, as illustrated for example in FIG. 18. It should be noted that the pressure exerting device 2000, illustrated in FIG. 19, is only exemplary. Any pressure exerting device 2000, which is configured to exert pressure on a fat phase removing device 100 according to embodiments described herein, is under the scope of the present invention.

According to yet another embodiment, the pushing press 2300, illustrated in FIG. 19, is configured to be accommodated in the space 906 of the bowl-like second pressing element 90. Furthermore, the pushing press 2300 is configured to press the bowl-like second pressing element 90 towards the bowl-like first pressing element 80, for pressing at least one adipose tissue 500, as described above.

According to still another embodiment, the pressure exerting device 2000 further comprises machinery for actuating the pushing press 2300 (not shown). According to yet a further embodiment, the pressure exerting device 2000 further comprises control elements as described above, for example but not limited to—a pressure control element, a velocity control element, a timer, and a temperature control element.

It should be noted that the configuration and orientation of the pressure exerting device 2000 as illustrated in FIG. 19 are only exemplary, and that other configurations and orientations of the pressure exerting device 2000 are under the scope of the present invention. For example, according to the embodiment illustrated in FIG. 19, the fat phase removing device holder 2200 is positioned under the pushing press 2300. However, an opposite orientation in which the fat phase removing device holder 2200 is positioned above the pushing press 2300 (not shown), is also under the scope of the present invention.

According to the embodiments illustrated in FIG. 1-19, the fat phase removing device 100 is configured to press at least one adipose tissue 500 in order to allow exit of a fat phase from the at least one adipose tissue 500. The common feature of these embodiments is removal of a fat phase from at least one adipose tissue by exerting an external pressure on the at least one adipose tissue. It should be noted though that other types of pressure exerted on the at least one adipose tissue are under the scope of the present invention, for example but not limited to, exerting a negative pressure on a fat phase of at least one adipose tissue.

According to another embodiment, of exerting a negative pressure on a fat phase of at least one adipose tissue, there is provided a sucking element configured to suck a fat phase from an adipose tissue. The sucking action exerts negative pressure on the fat phase and as a result the fat phase is removed from the adipose tissue. Any sucking element, which is configured to suck a fat phase from an adipose tissue, is under the scope of the present invention, for example but not limited to, a syringe, a cannula fluidically connected to a vacuum pump, and the like.

According to one embodiment, the sucking element is configured to independently remove a fat phase from at least one adipose tissue. For example, according to some embodiments, a cannula fluidically connected to a vacuum pump may penetrate the at least one adipose tissue, thus facilitating access to a fat phase in the at least one adipose tissue, and removal of the fat phase, by the cannula fluidically connected to a vacuum pump.

According to another embodiment, the sucking element is configured to remove a fat phase from at least one adipose tissue in combination with another element, for example but not limited to, a perforating element. According to this embodiment, a perforating element as disclosed herein is used to perforate at least one adipose tissue, thus facilitating access for the sucking element to reach the fat phase of the at least one adipose tissue and remove the fat phase from the at least one adipose tissue.

According to another aspect of the present invention, there is provided a method for preparing a preparation comprising a fat-depleted adipose tissue, the method comprises mechanically removing a fat phase from at least one adipose tissue.

At least one adipose tissue is provided from an animal. Any method known in the art for providing an adipose tissue from an animal is under the scope of the present invention, for example but not limited to, aspiration of subcutaneous adipose tissue.

According to one embodiment, in the method for preparing a preparation comprising a fat-depleted adipose tissue, the removing a fat phase from at least one adipose tissue comprises homogenizing the adipose tissue and extracting a fat-depleted adipose tissue from the homogenate. The homogenization of the adipose tissue is performed, for example but not limited to, by using a homogenizer. The extraction of the fat-free adipose tissue from the homogenate is performed, for example but not limited to, by centrifuging the homogenate. After centrifugation there phases are obtained—a lower aqueous phase comprising inter-cellular fluids, a middle cellular phase comprising cells derived from the adipose tissue, and an upper fatty phase comprising for example triglycerides. The middle cellular phase is a homogenized fat-depleted adipose tissue. Separation of the cellular phase from the lower phase and the upper phase is performed by any method known in the art for separating a cellular phase from a other phases, for example but not limited to, aspiration of the cellular phase with a syringe, or pipette, or a cannula fluidically connected to a pump; and filtering through a substrate configured to allow passage of an aqueous phase and a fatty phase, but not allow passage of a cellular phase. Examples of such a substrate include, but not limited to, a membrane, a gauze and the like.

According to another embodiment, in the method for preparing a preparation comprising a fat-free adipose tissue, the removing a fat phase from at least one adipose tissue comprises pressing the at least one adipose tissue.

According to yet another embodiment, in the method for preparing a preparation comprising a fat-free adipose tissue, the pressing the at least one adipose tissue comprises pressing the at least one adipose tissue between a first pressing element and a second pressing element. Any embodiment known in the art of pressing the at least one adipose tissue between a first pressing element and a second pressing element, including embodiments disclosed herein, is under the scope of the present invention.

It should be noted that pressing the at least one adipose tissue by using at least one hand palm of a user is also under the scope of the present invention, including but not limited to, pressing the at least one adipose tissue with a hand palm against a surface, like a table surface; and pressing the at least one adipose tissue between to hand palms.

According to yet another embodiment, in the method for preparing a preparation comprising a fat-free adipose tissue, the pressing the at least one adipose tissue comprises sucking the fat phase from the at least one adipose tissue. Any embodiment known in the art of sucking a fat phase from at least one adipose tissue, including embodiments disclosed herein, is under the scope of the present invention.

According to still another embodiment, the method for preparing a preparation comprising a fat-depleted adipose tissue further comprises perforating the at least one adipose tissue. According to some embodiments, the perforating the at least one adipose tissue is before the removing a fat phase from at least one adipose tissue. According to some other embodiments, the perforating the at least one adipose tissue is during the removing a fat phase from at least one adipose tissue. Any embodiment known in the art of perforating at least one adipose tissue, before or during the removing of the fat phase from the adipose tissue, including embodiments disclosed herein, is under the scope of the present invention.

According to a further embodiment, the method for preparing a preparation comprising a fat-depleted adipose tissue further comprises controlling a pressure which is applied on the at least one adipose tissue during pressing. Any embodiment known in the art for controlling a pressure during pressing of at least one adipose tissue, including embodiments disclosed herein, is under the scope of the present invention.

According to yet a further embodiment, the method for preparing a preparation comprising a fat-depleted adipose tissue further comprises controlling a velocity of a movement of any one of the first pressing element and the second pressing element, or both, during the pressing of the at least one adipose tissue. Any embodiment known in the art for controlling the velocity of the movement of any one of the first pressing element and the second pressing element, or both, including embodiments disclosed herein, is under the scope of the present invention.

According to still a further embodiment, the method for preparing a preparation comprising a fat-depleted adipose tissue further comprises controlling a time period of pressing the at least one adipose tissue. Any embodiment known in the art of controlling the time period of pressing at least one adipose tissue, including embodiments disclosed herein, is under the scope of the present invention.

According to an additional embodiment, the method for preparing a preparation comprising a fat-depleted adipose tissue further comprises controlling a temperature under which the at least one adipose tissue is pressed. Any embodiment known in the art of controlling the temperature under which the at least one adipose tissue is pressed, including embodiments disclosed herein, is under the scope of the present invention.

According to one embodiment, the at least one adipose tissue is pressed under ambient temperature. According to another embodiment, the at least one adipose tissue is pressed under a temperature in the range of substantially 18-28° C. According to a preferred embodiment, the at least one adipose tissue is pressed under a temperature in the range of substantially 37-40° C.

According to some embodiments, in the method for preparing a preparation comprising a fat-depleted adipose tissue, the fat-depleted adipose tissue is configured, without any further manipulation or treatment, to be transplanted or injected in a patient with a need for soft tissue regeneration, for example but not limited to, lack of soft tissue in the mouse cavity and in areas of receding gums. Furthermore, the fat-depleted adipose tissue of the present invention is configured, without any further manipulation or treatment, to serve as a dental regenerative membrane in dental surgery or oral surgery, or as a graft for treating skin defects.

In order to increase the efficiency of soft tissue regeneration with the fat-free adipose tissue of the present invention, according to some embodiments, the method for preparing a preparation comprising a fat-depleted adipose tissue further comprises adding a preparation rich in growth factors which is configured to enhance proliferation and differentiation of mesenchymal stem cells. Any preparation known in the art, which is rich in growth factors that are configured to enhance proliferation and differentiation of mesenchymal stem cells is under the scope of the present invention, for example but not limited to, platelet-rich fibrin, platelet-rich plasma, platelet-rich growth factor, plasma-rich growth factor, concentrated growth factors, and any combination thereof.

According to one embodiment, the preparation rich in growth factors is added to a fat-free adipose tissue which was pressed, for example but not limited to, a fat-free adipose tissue which was pressed with the pressing device illustrated in FIGS. 1, 2, 6, 7, 11 and 14. According to a preferred embodiment, the preparation rich in growth factors is added to a fat-free adipose tissue which was perforated and pressed, for example but not limited to, a fat-free adipose tissue which was perforated and pressed with the pressing device illustrated in FIGS. 3-5, 8-10, 12-13 and 18. The perforation of the fat-free adipose tissue facilitates entry of the preparation rich in growth factors into the fat-free adipose tissue, thus increasing the efficiency of the effect of the preparation rich in growth factors.

According to some embodiments, in the method for preparing a preparation comprising a fat-depleted adipose tissue, the fat-depleted adipose tissue is configured to be transplanted or injected in a patient with a need for bone tissue regeneration. Examples of situations in which there is a need for bone tissue regeneration are detailed in the "Background of the Invention".

Thus, according to one embodiment, the method for preparing a preparation comprising a fat-depleted adipose tissue further comprises adding at least one type of bone tissue to the fat-free adipose tissue. Any type of bone tissue known in the art is under the scope of the present invention. According to another embodiment, the method for preparing a preparation comprising a fat-depleted adipose tissue further comprises adding at least one bone substitute to the fat-free adipose tissue. Any bone substitute known in the art is under the scope of the present invention. According to yet another embodiment, the method for preparing a preparation comprising a fat-depleted adipose tissue further comprises adding at least one type of bone tissue and at least one bone substitute.

According to another embodiment, the method for preparing a preparation comprising a fat-depleted adipose tissue further comprises adding a preparation rich in growth factors which is configured to enhance proliferation and differentiation of mesenchymal stem cells, and adding at least one type of bone tissue to the fat-free adipose tissue. The adding a preparation rich in growth factors which is configured to enhance proliferation and differentiation of mesenchymal stem cells is according to embodiments described above.

According to a preferred embodiment, the at least one type of bone tissue and/or the at least one bone substitute, with or without the preparation rich in growth factors which is configured to enhance proliferation and differentiation of mesenchymal stem cells, are mixed with the fat-depleted adipose tissue, for example but not limited to, by using a mixer. According to another preferred embodiment the mixing with a mixer is for a period of time in the range of substantially 5-10 minutes. According to yet another preferred embodiment, the mixing is until the mixture is homogeneous. According to still another preferred embodiment, the mixing is until the mixture is semi-solid and suitable for transplantation as a bone graft.

According to yet another aspect of the present invention, a preparation comprising a fat-depleted adipose tissue, configured to be transplanted or injected in a patient with a need for soft tissue or bone regeneration, is provided.

According to one embodiment, the fat-depleted adipose tissue is prepared by mechanically removing a fat phase from at least one adipose tissue, according to any embodiment known in the art, including embodiments disclosed herein.

According to another embodiment, the preparation comprises a fat-depleted adipose tissue and a preparation rich in growth factors which is configured to enhance proliferation and differentiation of mesenchymal stem cells.

According to yet another embodiment, the preparation comprises a fat-depleted adipose tissue and at least one type of bone tissue.

According to still another embodiment, the preparation comprises a fat-depleted adipose tissue and at least one bone substitute.

According to a further embodiment, the preparation comprises a fat-depleted adipose tissue, at least one type of bone tissue and at least one bone substitute.

According to yet a further embodiment, the preparation comprises a fat-depleted adipose tissue, a preparation rich in growth factors which is configured to enhance proliferation and differentiation of mesenchymal stem cells and at least one type of bone tissue.

According to still a further embodiment, the preparation comprises a fat-depleted adipose tissue, a preparation rich in growth factors which is configured to enhance proliferation and differentiation of mesenchymal stem cells and at least one bone substitute.

According to an additional embodiment, the preparation comprises a fat-depleted adipose tissue, a preparation rich in growth factors which is configured to enhance proliferation and differentiation of mesenchymal stem cells, at least one type of bone tissue, and at least one bone substitute.

It should be noted that any one of the components of the preparation configured to be transplanted or injected in a patient with a need for soft tissue or bone regeneration, according to embodiments disclosed herein, namely the fat-depleted adipose tissue, the preparation rich in growth factors which is configured to enhance proliferation and differentiation of mesenchymal stem cells, the at least one type of bone tissue, and the at least one bone substitute—are prepared according to embodiments known in art, including embodiments disclosed herein.

It should be further noted, that usage of the device for preparing a preparation comprising a fat-depleted adipose tissue of the present invention, and the method for preparing a preparation comprising a fat-depleted adipose tissue of the present invention—significantly shorten in time and simplify the preparation of a preparation configured to be transplanted or injected in a patient with a need for soft tissue or bone regeneration. The currently available methods involve for example enzymatic treatment of the adipose tissue, which burdens the preparation process; or require prolonged incubation times, which prolong the preparation time in the scale of days and weeks. Furthermore, the currently available methods require the usage of special laboratory equipment, for example incubators. On the other hand, the present invention provides a device which is very simple to operate and less expensive. In addition, the present invention provides a much faster method for preparing the preparation. For example, the method for preparing a preparation configured to be transplanted or injected in a patient with a need for soft tissue regeneration lasts for up to substantially half an hour, and the method for preparing a preparation configured to be transplanted or injected in a patient with a need for bone regeneration lasts for up to substantially an hour. Furthermore, the preparation provided by the present invention shortens the regeneration and repair time of a soft tissue or a bone following transplantation or injection, as well as increases the success rate of clinical procedures involving the usage of the preparation of the present invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A device configured to mechanically remove a fat phase from at least one adipose tissue and prepare adipose derived mesenchymal stem cells, the device comprising:
   a first pressing element and a second pressing element, for pressing the at least one adipose tissue therebetween and forcing out at least part of the fat phase from the at least one adipose tissue when the pressing elements are moved toward one another; and
   a distance controlling element configured to maintain a gap between the first pressing element and the second pressing element during pressing of the at least one adipose tissue to avoid over-pressing or crushing of the at least one adipose tissue to prevent damage to the adipose derived mesenchymal stem cells,
   wherein the size of the gap is controlled to be correlated to the size of the at least one adipose tissue pressed therebetween, and wherein the gap has a size of less than 500 μm.

2. The device according to claim 1, further comprising a fat phase separating element.

3. The device according to claim 2, wherein the fat phase separating element is a sucking element.

4. The device according to claim 2, wherein the fat phase separating element is a drainage element.

5. The device according to claim 1, further comprising at least one perforating element attached to one of the first pressing element, the second pressing element, or to both pressing elements, wherein the at least one perforating element is configured to perforate the at least one adipose tissue placed in the gap and facilitate exit of the fat phase from the at least one adipose tissue.

6. The device according to claim 1, wherein at least one of the pressing elements is substantially flat.

7. The device according to claim 1, further comprising a temperature control element configured to control a temperature under which the at least one adipose tissue is pressed.

8. The device according to claim 7, wherein the temperature is in the range of substantially 37-42° C.

9. The device according to claim 1, wherein the first pressing element is stationary.

10. The device according to claim 5, wherein the at least one perforating element comprises at least one tooth-like structure that is attached to a surface of the first pressing element, or the second pressing element, or both the first pressing element and the second pressing element.

11. The device according to claim 1, wherein the first pressing element has a bowl-like structure having a space, and the second pressing element has a bowl-like structure that is configured to be accommodated in the space of the first bowl-like pressing element.

12. The device according to claim 1, further comprising a pressing and perforating unit configured to be provided between the first pressing element and the second pressing element, wherein the pressing and perforating unit comprises:
   a frame having a first surface facing the gap and configured to be in contact with the at least one adipose tissue, wherein the frame encloses a lattice of a plurality of crossed strips defining a plurality of lattice spaces; and
   at least one perforating member attached to the cross strips and configured to extend from the lattice spaces to beyond the first surface so as to perforate the at least one adipose tissue that is placed on top of the first surface.

13. The device according to claim 12, wherein the perforating member comprising:
   a tip pointing toward the gap;
   a leg attached to the tip, and configured to connect to one of the pressing elements; and
   a resilient connector connecting the tip to the strip so as to allow movements of the tip from the lattice spaced to beyond the first surface and vice versa.

* * * * *